(12) United States Patent
Colonna de Lega

(10) Patent No.: US 8,649,024 B2
(45) Date of Patent: Feb. 11, 2014

(54) NON-CONTACT SURFACE CHARACTERIZATION USING MODULATED ILLUMINATION

(75) Inventor: Xavier M. Colonna de Lega, Middlefield, CT (US)

(73) Assignee: Zygo Corporation, Middlefield, CT (US)

( * ) Notice: Subject to any disclaimer, the term of this patent is extended or adjusted under 35 U.S.C. 154(b) by 251 days.

(21) Appl. No.: 13/309,244

(22) Filed: Dec. 1, 2011

(65) Prior Publication Data

US 2012/0140243 A1    Jun. 7, 2012

Related U.S. Application Data

(60) Provisional application No. 61/419,386, filed on Dec. 3, 2010.

(51) Int. Cl.
*G01B 11/30* (2006.01)
*G01B 11/24* (2006.01)
*G06K 9/00* (2006.01)

(52) U.S. Cl.
USPC ............ 356/609; 356/601; 356/610; 382/154

(58) Field of Classification Search
None
See application file for complete search history.

(56) References Cited

U.S. PATENT DOCUMENTS

| | | | |
|---|---|---|---|
| 4,629,324 A | 12/1986 | Stern | |
| 5,151,609 A | 9/1992 | Nakagawa et al. | |
| 5,398,113 A | 3/1995 | De Groot | |
| 6,239,909 B1 | 5/2001 | Hayashi et al. | |
| 6,376,818 B1 | 4/2002 | Wilson et al. | |
| 6,483,641 B1 * | 11/2002 | MacAulay | 359/385 |
| 6,504,605 B1 * | 1/2003 | Pedersen et al. | 356/141.1 |
| 6,940,609 B2 * | 9/2005 | Scheiner | 356/605 |
| 6,943,968 B2 * | 9/2005 | Nielson et al. | 359/822 |
| 7,321,431 B2 | 1/2008 | De Groot | |

(Continued)

FOREIGN PATENT DOCUMENTS

| | | |
|---|---|---|
| EP | 1 935 620 | 6/2008 |
| KR | 10 2011 0029475 | 3/2011 |
| WO | WO 2008/151266 | 12/2008 |
| WO | WO 2009/149178 | 12/2009 |

OTHER PUBLICATIONS

Notification of Transmittal of the International Search Report and the Written Opinion of the International Searching Authority for International Application No. PCT/US2011/064417 dated Jul. 29, 2013.

(Continued)

*Primary Examiner* — Gordon J Stock, Jr.
(74) *Attorney, Agent, or Firm* — Fish & Richardson P.C.

(57) ABSTRACT

Methods for forming a three-dimensional image of a test object include directing light to a surface of best-focus of an imaging optic, where the light has an intensity modulation in at least one direction in the surface of best-focus, scanning a test object relative to the imaging optic so that a surface of the measurement object passes through the surface of best-focus of the imaging optic as the test object is scanned, acquiring, for each of a series of positions of the test object during the scan, a single image of the measurement object using the imaging optic, in which the intensity modulation of the light in the surface of best-focus is different for successive images, and forming a three-dimensional image of the test object based on the acquired images.

38 Claims, 18 Drawing Sheets

(56) References Cited

U.S. PATENT DOCUMENTS

| | | | |
|---|---|---|---|
| 7,729,049 B2 | 6/2010 | Xu et al. | |
| 7,978,346 B1 | 7/2011 | Riza | |
| 8,184,298 B2 * | 5/2012 | Popescu et al. | 356/450 |
| 8,237,835 B1 * | 8/2012 | Muller | 348/296 |
| 8,446,595 B2 * | 5/2013 | Ertl | 356/610 |
| 2008/0221837 A1 | 9/2008 | De Groot | |

OTHER PUBLICATIONS

K. Engelhardt and G. Haüsler, "Acquisition of 3-D data by focus sensing," Appl.Opt. 27: 4684-4689 (1988).

M. A. A. Neil, R. Juskaitis, and T. Wilson, "Method of obtaining optical sectioning by using light structured light in a conventional microscope," Opt. Lett. 22:1905-1907 (1997).

P. A. Stokseth, "Properties of a Defocused Optical System," JOSA 59:1314-1321 (1969).

M. Takeda et al., "Absolute three-dimensional shape measurements using coaxial and coimage plane optical systems and Fourier fringe analysis for focus detection," Opt. Eng. 39:61-68 (2000).

P. de Groot and al. "Determination of fringe order in white-light interference microscopy," Appl. Opt. 41, 4571-4578 (2002).

Juhasz et al., "The femtoseconde blade: applications in corneal surgery," Optics and Photonics News, Jan. 24-29, 2002.

* cited by examiner

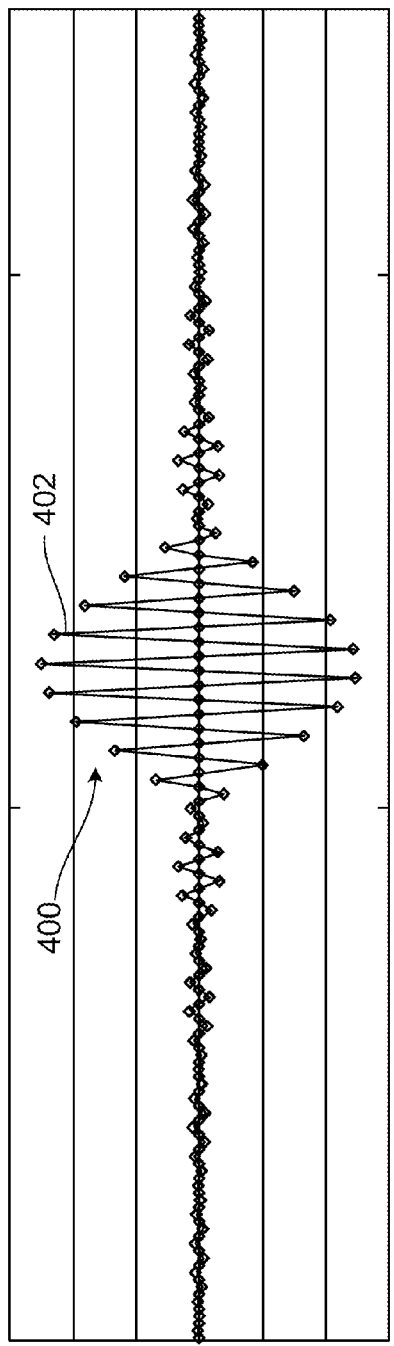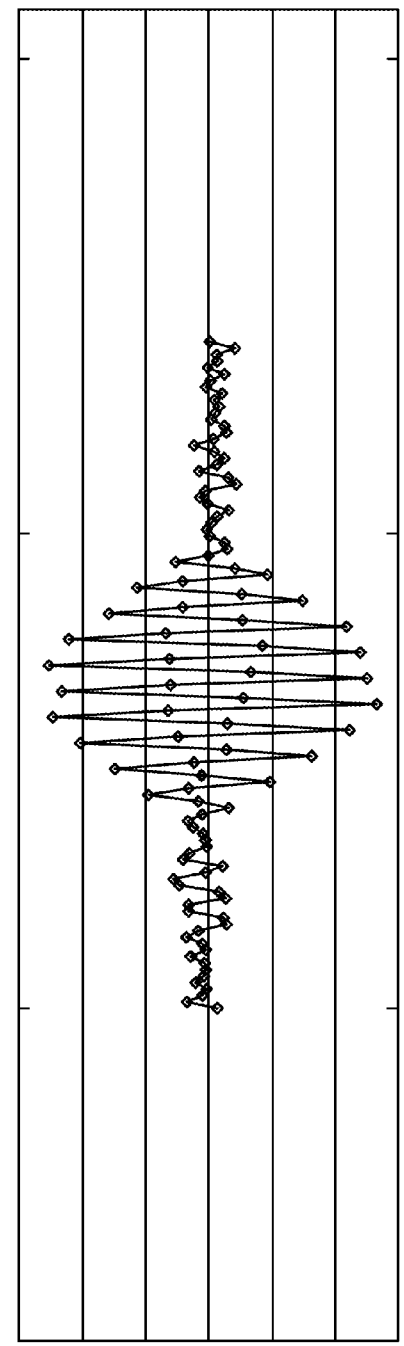

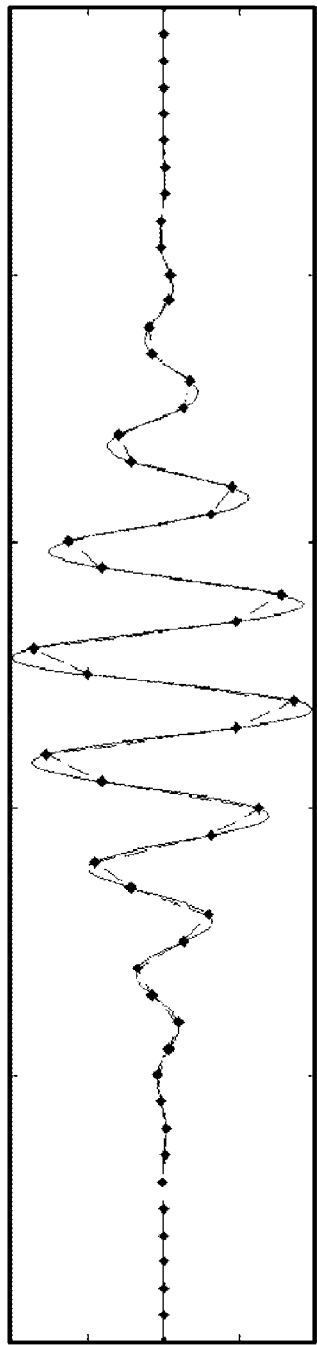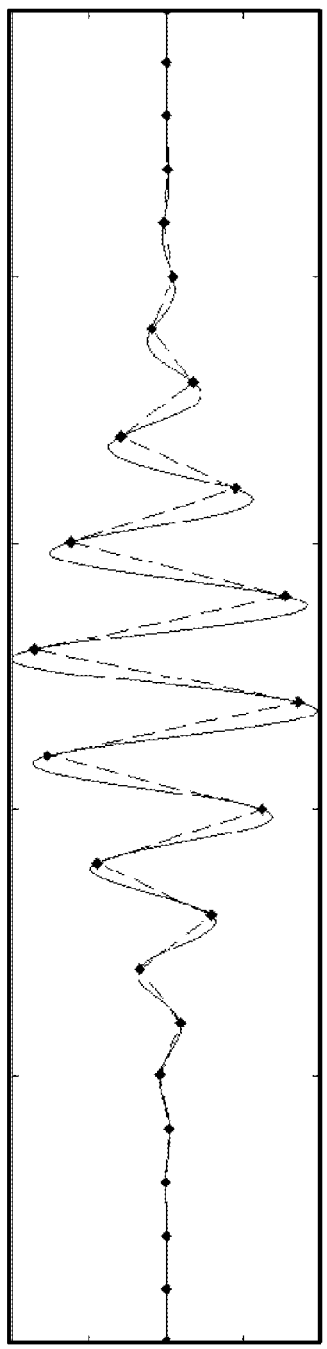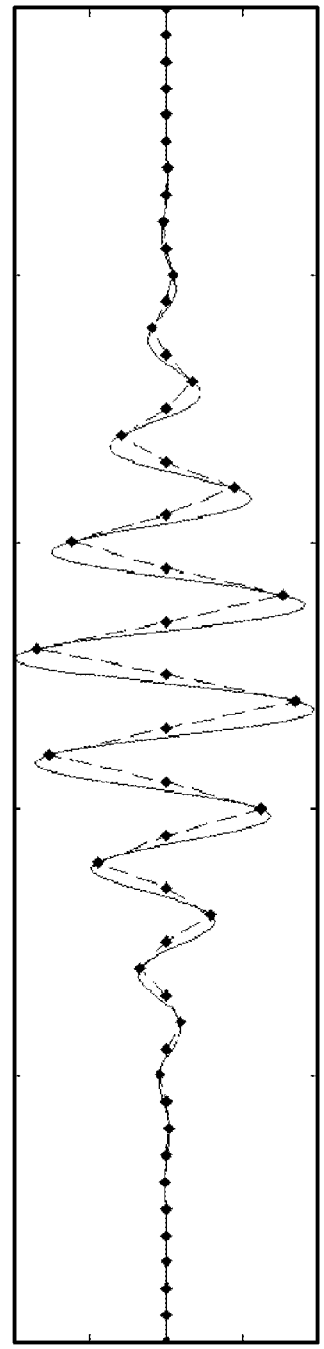

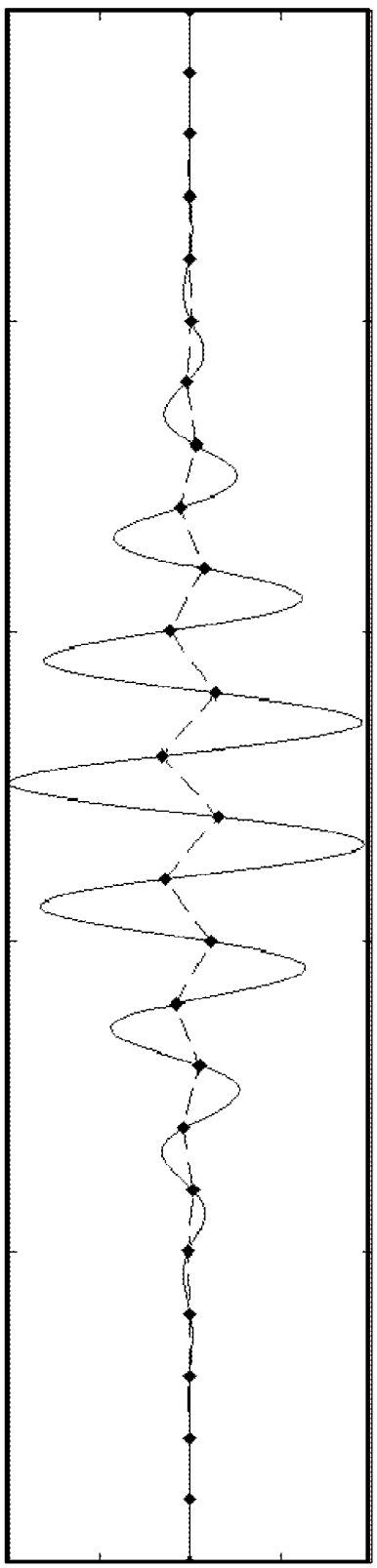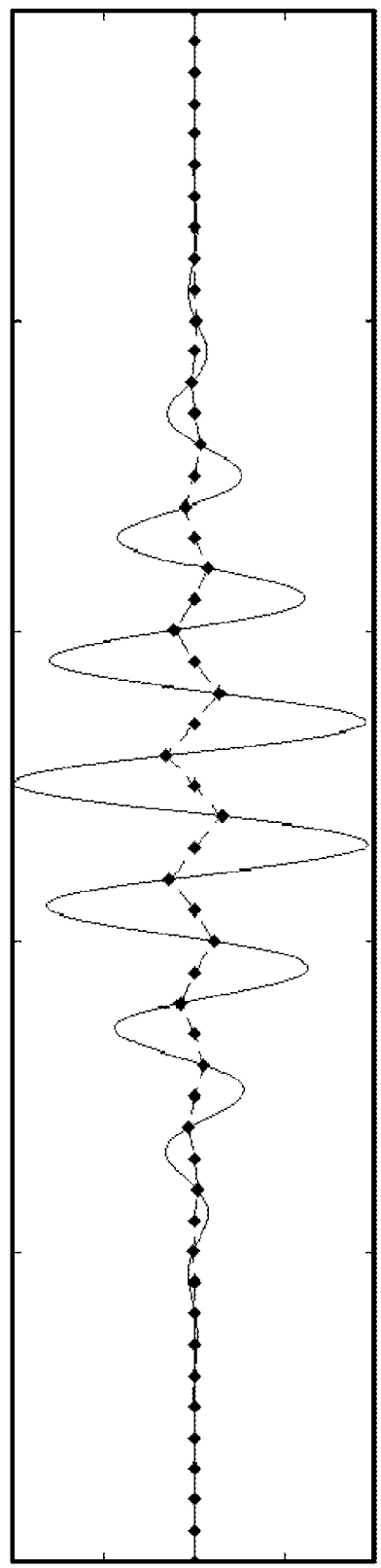

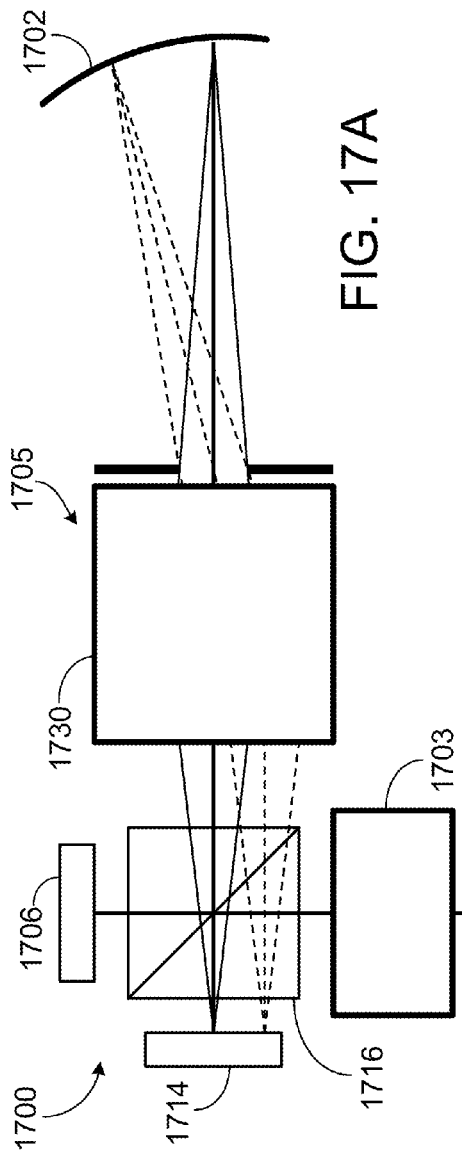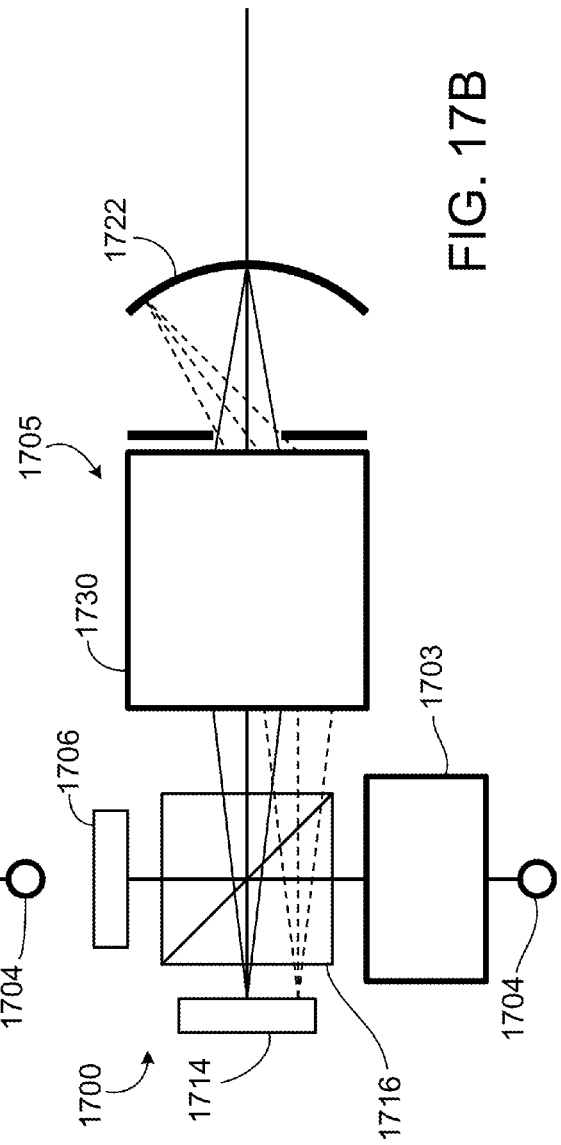

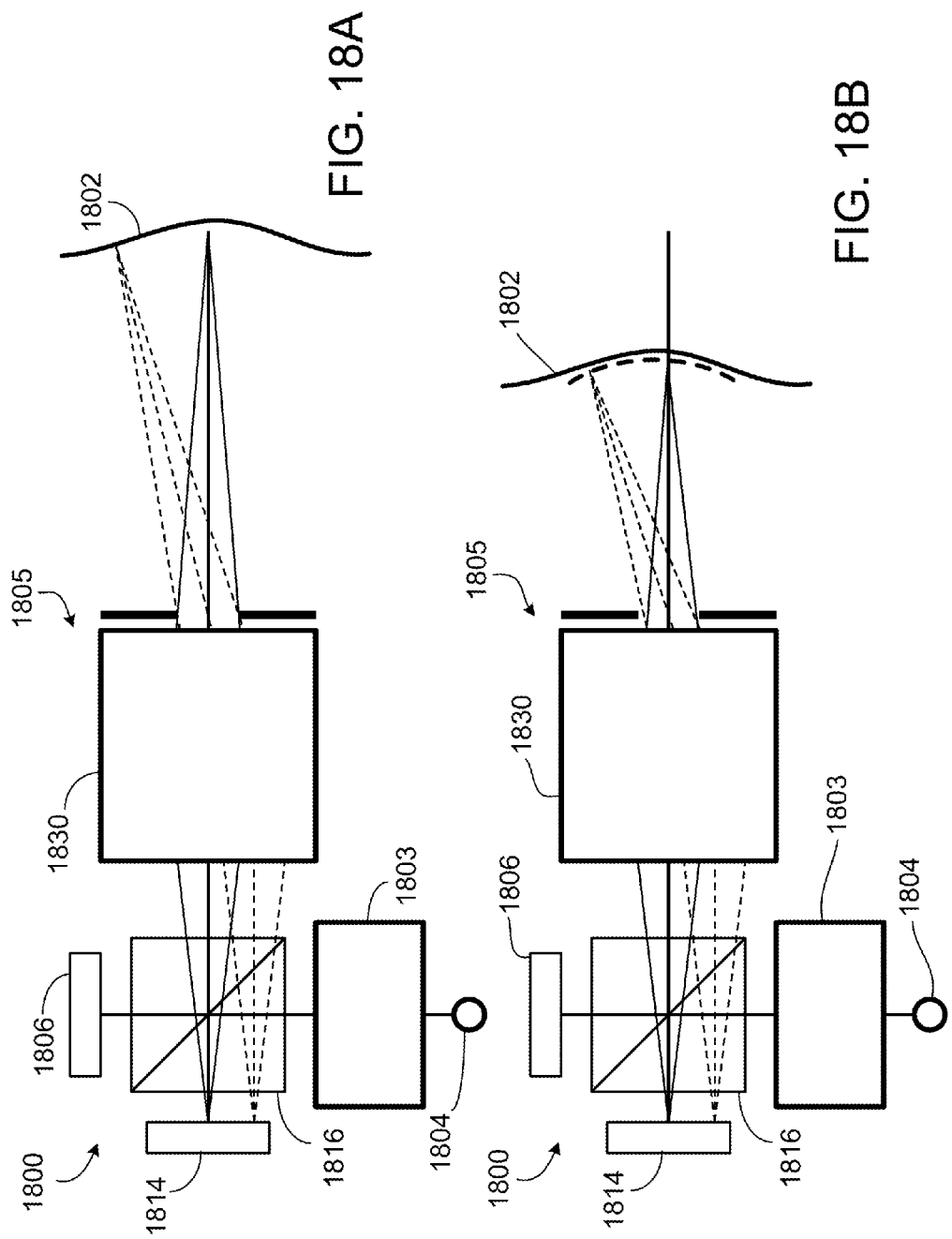

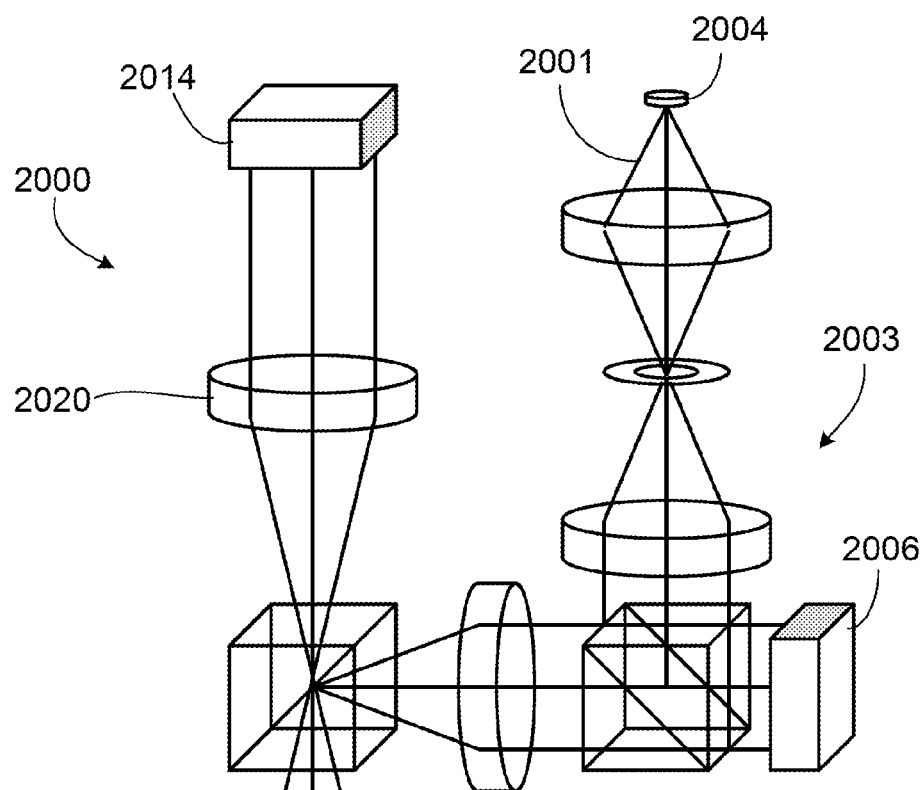
FIG. 20
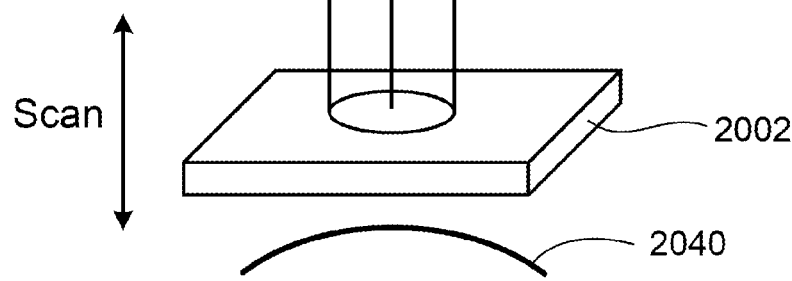

NON-CONTACT SURFACE CHARACTERIZATION USING MODULATED ILLUMINATION

CROSS REFERENCE TO RELATED APPLICATIONS

This application claims benefit of provisional patent application No. 61/419,386, entitled "Non-Contact Surface Characterization Using Modulated Illumination," filed on Dec. 3, 2010, the entire contents of which are hereby incorporated by reference.

TECHNICAL FIELD

This disclosure relates to methods of non-contact surface characterization using modulated illumination and devices configured to perform the same.

BACKGROUND

The field of non-contact surface characterization includes characterization and/or measurement of information about an object's surface including, for example, shape and surface finish measurements. Tools capable of non-contact surface characterization can be useful in manufacturing during stages such as process development, quality control and process control on the production floor. Non-contact surface characterization methods can include obtaining information about the three-dimensional (3D) shape and location of an object by analyzing the frequency content of an image of the object in an optical system.

SUMMARY

In general, the subject matter described in this specification relates to methods and systems for obtaining information about a surface of an object. The methods disclosed can include, for example, directing a structured illumination pattern to a surface of best-focus of an imaging optic while imaging a field in the surface of best-focus onto a multi-element detector. A structured illumination pattern is a non-uniform illumination pattern that contains some form of encoding based on light intensity. Examples of structured illumination patterns include periodic intensity patterns (e.g., modulated in one or two dimensions). An object is scanned through the surface of best-focus while a series of images of the illumination patterns on the object surface are sequentially acquired by the multi-element detector. For each successive image obtained, the illumination pattern is modified so that its intensity at each point in the field corresponding to a detector element is modulated from one frame to the next. The resulting signal acquired at each detector element has a modulation, with the maximum amplitude occurring at or near the position of the object surface as it intersects the surface of best-focus of the objective. Based on an analysis of the signals provided by the sequence of images, measurements of topography and surface texture of the object can be obtained and, in some implementations, a three-dimensional image of the object's surface can be produced.

In some embodiments, a detector plane and pattern-generating plane are mapped onto a surface in object space that is nominally conformal to the shape of the object to be characterized including, for example, a plane, a sphere, a parabola, a cylinder, a cone, or an aspheric optic.

In certain embodiments, the signal recorded at a pixel (i.e., element) on the detector has a modulation envelope that emulates some of the characteristics of a scanning low-coherence interferometer (SWLI) signal. Conversion of scan data to topography or reflectivity data may therefore be accomplished by application of envelope-detection algorithms developed for SWLI such as a frequency domain analysis ("FDA") or least squares analysis ("LSQ").

In some embodiments, the device used for creating the projected illumination pattern is programmable, which allows adapting the frequency content, orientation and spatial intensity distribution to optimize the measurement capability for a given object.

The structured illumination modulation scheme can be optimized to enable a fast autofocus scan of an optical system. An application in the context of laser eye surgery is the localization of the position of laser optics with respect to a critical component that makes contact with the cornea. Another application is rapid focusing of a low-coherence interferometer, in which case the autofocus scan rate is selected to average out the interference signal from the detected signal.

In certain embodiments, the apparatus presents to the user an enhanced image of the object that combines height information with additional surface information, such as color, absorption, texture, etc.

Various aspects of the subject matter described in this specification are summarized as follows.

In general, one aspect of the subject matter described in this specification can be embodied in methods for forming a three-dimensional image of a test object, in which the methods include directing light to a surface of best-focus of an imaging optic, where the light has an intensity modulation in at least one direction in the surface of best-focus, scanning a test object relative to the imaging optic so that a surface of the measurement object passes through the surface of best-focus of the imaging optic as the test object is scanned, acquiring, for each of a series of positions of the test object during the scan, a single image of the measurement object using the imaging optic, in which the intensity modulation of the light in the surface of best-focus is different for successive images, and forming a three-dimensional image of the test object based on the acquired images.

These and other embodiments can each optionally include one or more of the following features. For example, in some implementations, directing the light to the surface of best-focus includes imaging a spatial light modulator (SLM) to the surface of best-focus. The intensity modulation of the light in the surface of best-focus can be varied using the spatial light modulator.

In some implementations, directing the light to the surface of best-focus includes imaging a pattern-generating plane onto a surface in object space. The surface can be conformal to a shape of the test object. The shape of the test object can be planar, spherical, parabolic, cylindrical, conical, or aspheric.

In some implementations, the intensity modulation is a periodic modulation. The periodic modulation can be a sinusoidal modulation. The phase of the periodic modulation can be varied by less than $2\pi$ between each successive image. The phase of the periodic modulation can be varied by $\pi$ or less between each successive image. The phase of the periodic modulation can be varied by $\pi/2$ between each successive image.

In some implementations, the intensity modulation is a two-dimensional intensity modulation. The scan positions can be evenly spaced. The intensity modulation can be selected based on a slope of the test object surface.

In some implementations, forming the three-dimensional image includes identifying, for multiple different locations of the test object surface, the scan position corresponding to where each location intersects the surface of best-focus. An intensity of the acquired images as a function of scan position at each of the different locations can include an amplitude modulation. Identifying the scan position corresponding to where each location intersects the surface of best-focus can include identifying the scan position where a modulation amplitude is largest.

In some implementations, forming the three-dimensional image includes deriving an intensity signal for each of multiple different locations of the test object surface, each intensity signal corresponding to the intensity of the acquired images at the corresponding location as a function of scan position. Forming the three-dimensional image can include identifying a scan position corresponding to a maximum amplitude of a modulation of the intensity signal for each location. Identifying the scan position can include transforming each intensity signal into a frequency domain.

In some implementations, the test object is a lens element. The three-dimensional image can be, for example, a monochrome image. Alternatively, the three-dimensional image can be a color image.

In general, another aspect of the subject matter described in this specification can be embodied in methods for forming a three-dimensional image of a test object, in which the methods each include forming an image of a spatial light modulator at a surface of best-focus of an imaging optic, scanning a test object relative to the imaging optic so that a surface of the measurement object passes through a surface of best-focus of the imaging optic as the test object is scanned, acquiring, for each of a series of positions of the test object during the scan, a single image of the test object using the imaging optic, in which the spatial light modulator varies an intensity modulation in the light forming the image so that the modulation of the light at the surface of best-focus is different for successive images, and forming a three-dimensional image of the test object based on the acquired images.

In general, another aspect of the subject matter described in this specification can be embodied in methods for forming a three-dimensional image of a test object, in which the methods each include directing light to a surface of best-focus of an imaging optic, where the light has an intensity modulation in at least one direction in the surface of best-focus, scanning a test object relative to the imaging optic so that a surface of the measurement object passes through a surface of best-focus of the imaging optic as the test object is scanned, imaging the surface of best-focus to a multi-element detector, acquiring, for each of a series of positions of the test object during the scan, a single intensity measurement at one or more elements of the multi-element detector, in which the intensity modulation of the light in the surface of best-focus is different for successive positions of the test object during the scan, and forming a three-dimensional image of the test object based on the acquired intensity measurements.

In general, another aspect of the subject matter described in this specification can be embodied in systems for forming a three-dimensional image of a test object, in which the systems each include a microscope including an imaging optic, the imaging optic having a surface of best-focus, a spatial light modulator, one or more optical elements arranged to direct light from the spatial light modulator to form an image of the SLM at the surface of best-focus during operation of the system, a scanning stage arranged to scan the test object relative to the microscope object during operation of the system so that a surface of the test object intersects the surface of best-focus, a multi-element detector positioned relative to the microscope such that the microscope forms an image of a field at the surface of best-focus on the multi-element detector during operation of the system, and an electronic control module in communication with the scanning stage, the spatial light modulator, and the multi-element detector, in which during operation, the system causes the multi-element detector to acquire a single image of the test object for each of multiple scan positions of the test object relative to the imaging optic, causes the SLM to variably modulate the intensity of light at the surface of best-focus in at least one direction so that the intensity modulation of the light is different for successive images, and forms a three-dimensional image of the test object based on the acquired images.

This and other embodiments can each optionally include one or more of the following features. In some implementations, the system includes, for example, a light source arranged to direct light to the SLM during operation of the system. The SLM can be a reflective SLM or a transmissive SLM.

In some implementations, the SLM can be a liquid crystal panel, or include a micro-mirror array.

In some implementations, the imaging optic has a numerical aperture greater than 0.6, a numerical aperture greater than 0.8, a numerical aperture greater than 0.9, or a numerical aperture of 0.95.

In some implementations, the system further includes color filters arranged to filter the wavelength of light forming the images at the multi-element detector.

The one or more optical elements can include, for example, a fisheye lens, an endoscope, and/or a zoom lens.

Implementations disclosed herein can offer several advantages. For example, in some implementations, the methods and apparatus can be used to provide non-contact three-dimensional imaging of an object. The imaging can be performed using short measurement times and/or to achieve high resolution images of objects' surfaces. In some implementations, the imaging is performed with reduced sensitivity to environmental perturbations such as, for example, vibration or acoustic noise.

Implementations offer other advantages as well. For example, the methods and structures disclosed herein can, in some implementations, provide similar depth sectioning capabilities as a conventional confocal microscope. The use of structured illumination profiling can offer certain benefits compared to confocal microscopy (e.g., reduced source brightness requirements) and interference microscopy. For example, in some implementations, structured illumination has reduced source brightness requirements relative to conventional interference microscopes. Alternatively, or in addition, restrictions on which non-interferometric microscope objectives can be used can be reduced. For example, in some implementations, higher numerical aperture objectives are available relative to the objectives available in Michelson or Mirau interferometers.

The details of one or more embodiments are set forth in the accompanying drawings and the description below. Other features and advantages will be apparent from the description, drawings, and from the claims.

BRIEF DESCRIPTION OF DRAWINGS

FIG. 4 is a graph of a simulated light intensity signal.

FIG. 5 is a graph of an experimental intensity signal recorded by a pixel of an image-recording device.

FIGS. 8A-8B are plots of a simulated analog intensity signal overlaid with a corresponding digitized sampling of the intensity signal.

FIG. 8C is a plot of the simulated analog intensity signal of FIG. 8B overlaid with the corresponding digitized intensity signal of FIG. 8B, where zeros have been inserted into the digitized intensity signal.

FIG. 10A is a plot of a simulated analog intensity signal overlaid with a corresponding digitized sampling of the simulated intensity signal.

FIG. 10B is a plot of the simulated analog intensity signal of FIG. 10A overlaid with the digitized intensity signal of FIG. 10A, where zero values have been inserted into the digitized intensity signal.

FIGS. 17A-17B are schematic diagrams of exemplary imaging systems.

FIGS. 18A-18B are schematic diagrams of exemplary imaging systems.

FIG. 20 is a schematic of an exemplary system for performing laser eye surgery.

DETAILED DESCRIPTION

Acquiring the Light Intensity Signal

Figure 1:
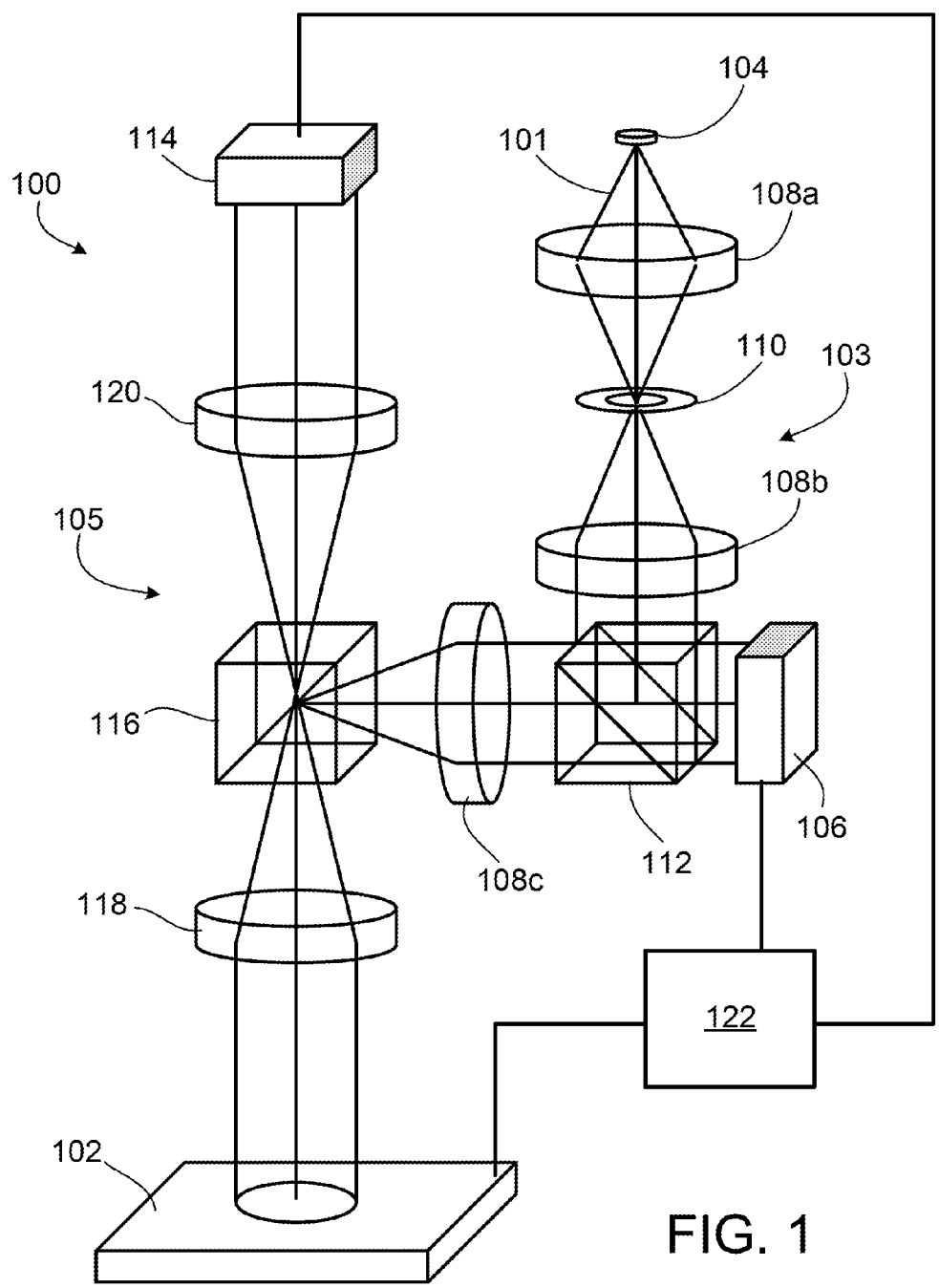
FIG. 1 is a schematic diagram of an exemplary system for providing a 3D image of a sample object.

FIG. 1 is a schematic diagram of an exemplary structured illumination system 100 for providing a 3D image of a sample object 102. An illumination portion 103 of the system 100 includes an illumination source 104, a spatial light modulator (SLM) 106, one or more lenses (108a-108c), an aperture 110 and a beam combiner 112. An imaging portion 105 of the system 100 includes an image-recording device 114, a beam splitter 116, an objective lens 118 and a tube lens 120. For the purposes of this disclosure, the coordinate system is defined such that the z-axis is parallel to the optical axis of the objective lens 118 and the x and y-axes are parallel to the lens' plane of best-focus such that xyz forms an orthogonal coordinate system.

During operation of the system 100, light 101 generated from the illumination source 104 passes through the lenses 108a, 108b and the aperture 110, where the light 101 then is incident on the beam splitter 112. Beam splitter 112 reflects a portion of the incident light 101 onto the SLM 106. In the present example, the SLM 106 is configured to modify and reflect the light incident on its surface so as to produce an illumination pattern characterized as either binary (i.e., the imaging pattern has regions where light is present and regions where light is absent) or quasi-continuous (i.e., the imaging pattern can be approximated by continuous varying levels of light intensity).

The illumination pattern reflected from the SLM 106 then passes through the beam splitter 112 and lens 108c to a second beam splitter 116 where the illumination pattern then is directed through the objective lens 118 and preferentially fills the back pupil of the objective 118. The illumination pattern is re-imaged in object space to the plane of best-focus (focal plane) of the objective lens 118. Light reflecting and/or scattering off a surface of the sample object 102 then proceeds through the objective lens 118, the beam splitter 116, and the tube lens 120 onto a light-detecting surface/plane of the image-recording device 114 where it is recorded. The recorded light thus acquired can be stored in digital format as an array of light intensity signals, with each light intensity signal being acquired from a corresponding pixel of the image-recording device 114.

During imaging, the object 102 is translated vertically with respect to the objective lens 118 (i.e., toward or away from the objective lens 118). The sample object 102 can be displaced or actuated by an electromechanical transducer (not shown) and associated drive electronics controlled by a computer 122 so as to enable precise scans along a direction of translation of the object 102. Examples of transducers include, but are not limited to, piezoelectric transducers (PZT), stepper motors and voice coils. Alternatively, or in addition, the objective lens 118 may be translated vertically with respect to a position of the sample object 102. Again, an electromechanical transducer and associated drive electronics may be used to control the translation. The image-recording device 114 simultaneously records imaging data as the object 102 is scanned through the plane of best-focus of the objective lens 118 such that multiple light intensity signals will be recorded over time. That is, an image of the object and illumination pattern is captured by the image-recording device in the form of the light intensity signal at corresponding scan positions. For example, if the image-recording device 114 includes a 128× 128 array of pixels and if 64 images are stored during a scan, then there will be approximately 16,000 light intensity signals each 64 data points in length. In some implementations, the scan positions are evenly spaced, i.e., the translation distance between successive images captured by the image-recording device is the same.

Furthermore, the SLM 106 spatially modulates the illumination pattern as the sample object 102 is translated, such that the object 102 is illuminated with a different pattern at different corresponding vertical positions of the scan. The continuous modification of the illumination pattern during the scan results in a modulated light intensity signal at each pixel of the image-recording device 114. After the data has been acquired, the computer 122 can process the light intensity signals in accordance with, for example, pattern matching techniques, and output data indicative of a surface topography of the sample object 102.

When a surface of the sample object 102 is located at the plane of best-focus of the objective 118, an in-focus image of the illumination pattern is formed on a surface of the object 102. The in-focus image exhibits the highest contrast achievable for a given illumination numerical aperture (NA) of the system 100. The intensity of the image of the object surface that is reflected back to the image-recording device 114 at each pixel is proportional to the product of the local object surface reflectivity and the local intensity of the projected illumination pattern. In contrast, when the surface of the object 102 is located away from the plane of best-focus of the objective lens 118, the image of the illumination pattern on the surface of the object 102 is blurred and thus exhibits reduced contrast. The image of the surface of the object 102 passing back through the objective lens 118 towards the image-recording device then is blurred again. The result is that the contrast of the projected illumination pattern, as seen on the image-recording device, is a function of the vertical displacement of the object surface with respect to the plane of best-focus of the objective. Accordingly, the depth profiling capability of the system 100 arises from the detection of the position of the object 102 for which the pattern contrast is a maximum at each pixel of the image-recording device 114, as the object 102 is scanned through the best-focus plane.

Figure 2:
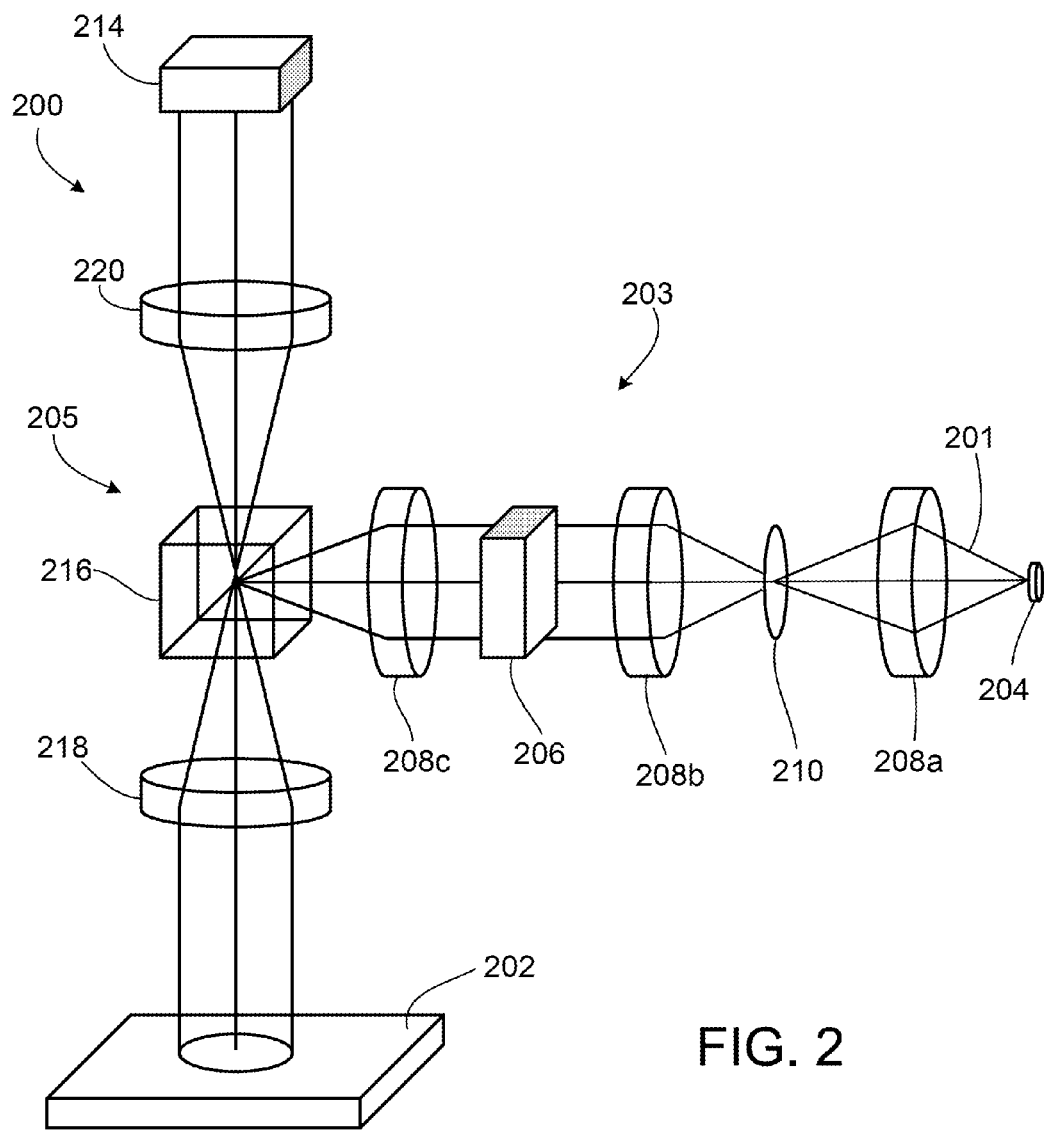
FIG. 2 is a schematic diagram of an exemplary system for providing a 3D image of a sample object.

In some implementations, the SLM 106 can be used in a transmission arrangement as opposed to reflection. For example, FIG. 2 shows an exemplary system 200 that includes the same components as system 100, except that a single beam splitter 216 is used in the arrangement and a SLM is configured to transmit incident light rather than reflect the incident light (computer 122 also is omitted for ease of viewing). In the example shown in FIG. 2, the transmission SLM 206 modifies incident light 201 generated by an illumination source 204 to produce a binary or quasi-continuous illumination pattern. The illumination pattern produced by the SLM 206 passes through a lens 208c and is incident on the beam splitter 216, where the pattern then is directed through an objective lens 218 and imaged onto a plane of best-focus for the objective. The illumination pattern reflects off a sample object 202 and passes back through the objective lens 218, the beam splitter 216, a tube lens 220 and is finally detected by a image-recording device 214. Similar to the system 100, the illumination pattern produced by the SLM 206 can be spatially modulated as the image data is acquired, such that different light intensity patterns are produced at corresponding different scan positions of the object.

In each of the foregoing examples, the illumination sources 104, 204 can include, but are not limited to, spectrally-broadband sources or narrow band sources. Examples of broadband sources include: an incandescent source, such as a halogen bulb or metal halide lamp, with or without spectral bandpass filters; a broadband laser diode; a light-emitting diode; a combination of several light sources of the same or different types; an arc lamp; any source in the visible spectral region (about 400 to 700 nm), any source in the IR spectral region (about 0.7 to 300 μm), any source in the UV spectral region (about 10 to 400 nm). For broadband applications, the source preferably has a net spectral bandwidth broader than 5% of the mean wavelength, or more preferably greater than 10%, 20%, 30%, or even 50% of the mean wavelength. The source may also include one or more diffuser elements to increase the spatial extent of the input light being emitted from the source. Examples of narrow band sources include a laser or a broadband source in combination with a narrowband filter.

The source can be a spatially-extended source or a point source. In some implementations, it is preferable to use a spatially-extended source (e.g., when the surface of an object being imaged is smooth) to avoid observing a high-contrast pattern regardless of the position of the object with respect to the plane of best focus. The image-recording devices 114, 214 can include a plurality of detector elements, e.g., pixels, arranged in at least one and more generally two dimensions. Examples of image-recording devices include digital cameras, multi-element charge coupled devices (CCDs) and complementary metal oxide semiconductor (CMOS) detectors. Other image-recording devices may be used as well. In some implementations, one or more color filters can be included in the system to filter the wavelength of light forming the images at the image-recording device. The one or more color filters can be arranged to be an integral component of the image-recording device or as separate from the image-recording device.

In some implementations, the objective lenses 118, 218 can be incorporated as components of any standard microscope. For example, the systems can include a microscope configured for use with one or more different objective lenses, each providing a different magnification. The NA of the objective lenses 118, 218 can be about 0.1 or greater (e.g., about 0.2 or greater, about 0.3 or greater, about 0.4 or greater, about 0.5 or greater, about 0.6 or greater, about 0.7 or greater, about 0.8 or greater, about 0.9 or greater, or about 0.95 or greater). Other NA values are possible as well.

Examples of SLMs that can be used to reflect light, similar to the arrangement shown in FIG. 1, include liquid crystal on silicon (LCOS) devices or micromirror array devices, e.g., a digital micromirror device (DMD). To spatially modulate illumination patterns produced by a LCOS device, a user can electronically control, using the appropriate hardware and software, the direction and amount of light reflected by each pixel of the LCOS device. Likewise, to spatially modulate the illumination pattern produced by a DMD, a user can electronically control the direction and/or orientation of each individual mirror to vary the amount of light reflected at each mirror. Examples of SLMs that can be used to transmit light, similar to the arrangement shown in FIG. 2 include liquid crystal device (LCD) modulators that can be electronically controlled to vary the amount of light transmitted. Alternatively, in some implementations, transmission SLMs can include intensity masks, such as gratings, Ronchi rulings, or other patterned surfaces that have regions of varying degrees of absorption for the wavelength of incident light. To spatially modulate the illumination patterns produced by the transmission SLMs formed from intensity masks, the SLMs can be mounted on a mechanical frame that provides controlled in-plane motion of the SLM. The motion of the frame can be provided using one or more mechanical or electronic actuators, including, for example, piezoelectric actuators, stepper-motors, or voice coils. Other SLMs can be used in transmission or reflection arrangements as well. In some implementations, an electronic controller may store in memory instructions for how to generate one or more illumination patterns. In some implementations, the SLM used for creating the projected pattern is programmable, such that the frequency content, orientation and spatial intensity distribution of a particular pattern can be optimized for measurement of a given object. It should be noted that the various structured illumination systems described in this disclosure are not restricted to any particular material or type of object, as long as at least some portion of the illumination light is redirected from the object surface back to the image-recording device.

Analyzing the Light Intensity Signal

Figure 3:
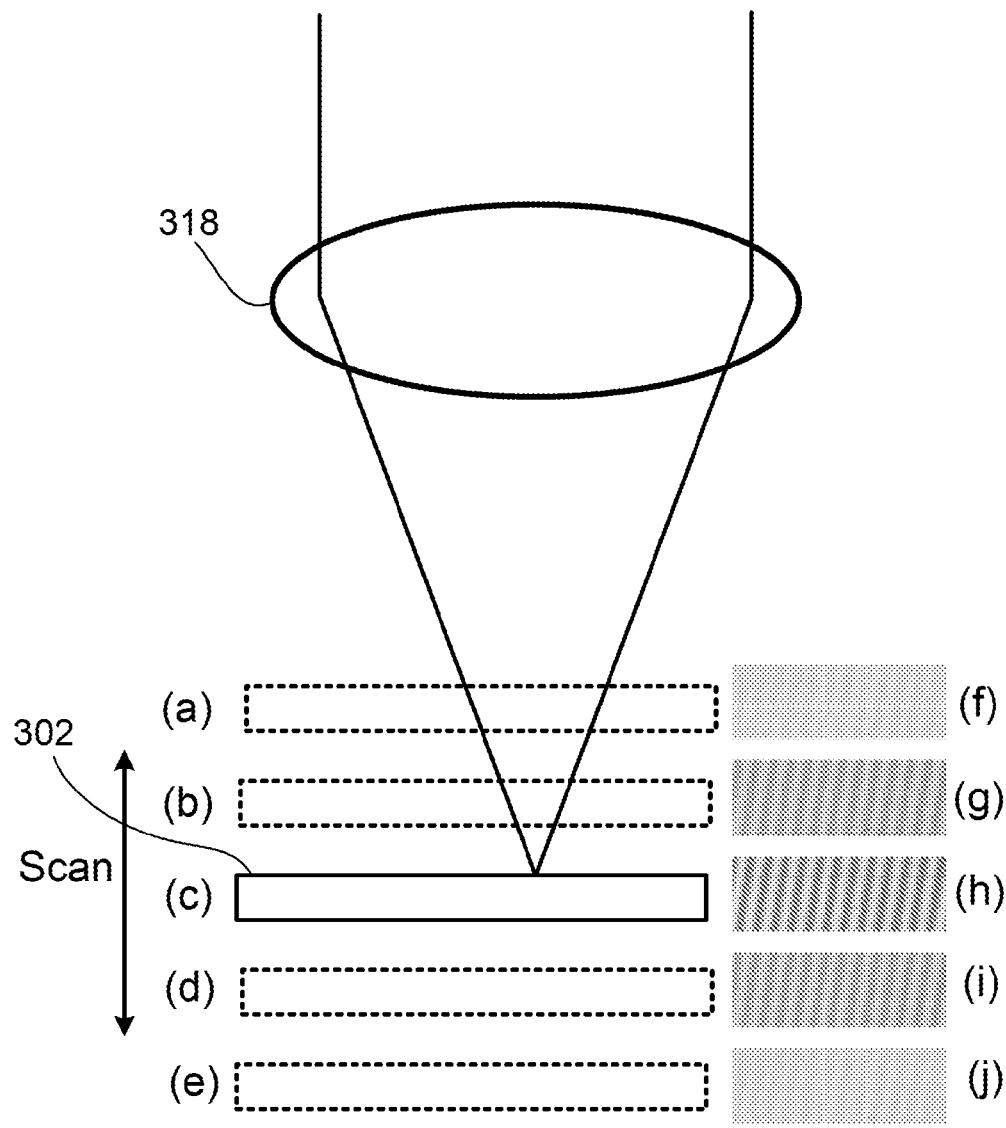
FIG. 3 is a schematic illustrating various scan positions of a sample object.

As explained above, in both exemplary systems, the contrast of the illumination pattern improves as a sample object is translated into the plane of best-focus, whereas the illumination pattern becomes blurred as the object moves away from the plane of best-focus. For example, FIG. 3 is a schematic illustrating various scan positions of a sample object 302. As shown in the schematic, the object 302 is scanned over multiple different vertical positions, (a)-(e), with respect to an objective lens 318. FIG. 3 also shows images (f)-(j) captured by an image-recording device of a top surface of a sample object at scan positions corresponding to positions (a)-(e). As shown in the images (f)-(j), the object 302 is illuminated with a binary image pattern that includes a series of equally spaced parallel lines. When the object 302 is located at the plane of best-focus of an objective lens 318, i.e., position (c), the pattern (h) illuminated on a surface of the sample object 302 exhibits the highest contrast for the NA of the objective lens 318. In contrast, when the sample object is vertically displaced to any one of positions (a), (b), (d), or (e), the illumination pattern imaged onto the surface of the sample object 302 exhibits reduced contrast and appears blurry. By detecting the position of the sample object 302 for which the contrast exhibited the illumination pattern is greatest at each pixel of the image-recording device, it is possible to characterize information about the surface of the object 302 including, for example, relative surface height, roughness, film thickness, reflectivity, and absorption, among other features.

To determine the position at which the contrast is greatest, the intensity modulation of the light in the focal plane is varied using the spatial light modulator such that different illumination patterns are projected on the object as the object is translated through the plane of best-focus. The projected pattern changes between image acquisitions so that a first frame of data corresponds to a first projected pattern, a second frame of data corresponds to a second projected pattern, etc. The system scans the object continuously during data acquisition. At the same time, the projected pattern can remain constant during frame integration (i.e., during the time period while each frame is acquired) when using a programmable SLM device (e.g., LCD or DMD), such that there is no contrast loss due to integration. The resulting temporal light intensity profile, as recorded by each pixel of an image-recording device, exhibits a bell-shaped amplitude modulated envelope, where the maximum value of the amplitude modulation can provide object topography information such as the height of the object surface.

As explained above, the projected pattern can be binary (i.e., the imaging pattern has regions where light is present and regions where light is absent) or quasi-continuous (i.e., the imaging pattern can be approximated by continuous varying levels of light intensity). The intensity modulation of light imaged onto the focal plane can include modulation along one or more dimensions. For example, the intensity modulation of light can produce one-dimensional patterns (i.e., patterns that vary along one direction but are uniform in another orthogonal direction) such as square-wave patterns, sawtooth patterns, or sinusoidal patterns, among others. In some implementations, the illumination patterns produced by light intensity modulation include two-dimensional patterns that vary in both a first direction and a second orthogonal direction (e.g., a checkerboard pattern). The intensity modulation of light imaged onto the focal plane can be periodic or non-periodic. In some implementations, the periodic modulation includes a sinusoidal modulation. In some implementations, the phase-shift of the illumination pattern can be a function of the position of the scan position. The phase of the periodic modulation can be varied by less than $2\pi$ between each successive image, by $\pi$ or less between each successive image, or by $\pi/2$ between each successive image. Multiple illumination patterns can be combined into a single pattern that is projected onto the sample object, where each of the patterns in the combination is different or has a different phase shift. Other phase variations and illumination patterns are possible as well. The illumination patterns to be projected onto the object can be stored electronically as data in a memory device of an electronic controller, where the electronic controller is capable of converting the data into electrical signals for altering operation of the SLM.

In an example implementation, the projected pattern is sinusoidal along the x-direction on the object surface and uniform along the y-direction. The projected illumination pattern during image acquisition can be described by the following equation:

$$P(x, y, n) = 1 + \cos\left(\frac{2\pi}{\Lambda}x + n\Delta\varphi\right) \quad (1)$$

where n indicates the n-th pattern projected during the image acquisition sequence, $\Delta\varphi$ is the phase increment between successive patterns in the sequence, and $\Lambda$ is the period of the pattern (i.e., the pattern pitch). Depending on the means of modulating the illumination pattern, it can be advantageous to select a phase increment that is an integer fraction of $2\pi$. For example, in the case of periodic modulation, only four 90-degree phase shifted images for the SLM would need to be stored, thus reducing the amount of memory required for the system.

As the sample object moves out of focus, the pattern contrast seen by the image-recording device is reduced. The observed contrast is in practice a function of the pattern pitch $\Lambda$ in object space, the NA of the objective lens, the mean wavelength $\lambda$ of the illumination light and the object surface defocus z (i.e., the distance from the object surface to the best-focus position of the optics). An approximation for computing the contrast (or normalized modulation) as a function of normalized defocus u is given as $$V(u) = \left|(1 - 0.69v + 0.0067v^2 + 0.043v^3)2\frac{J1(uv(2-v))}{uv(2-v)}\right| \quad (2)$$

$$u = \frac{8\pi}{\lambda}z\sin\left(\frac{\sin^{-1}NA}{2}\right)^2$$

$$v = \frac{\lambda}{\Lambda NA}$$

where J1 is the first-order Bessel function of the first kind.

FIG. 4 is a graph of a simulated light intensity signal as would be observed by a single pixel of an image-recording device when an object having a smooth surface is scanned through an in-plane focus of an objective while a pattern of the form described by Eq. (1) is projected onto the object's surface. The vertical axis represents the light intensity whereas the horizontal axis corresponds to the time over which the signal was recorded. The simulated intensity signal was produced using the mathematical modeling software MathCAD®. The pattern used to obtain the simulated light intensity signal shown in FIG. 4 has a phase increment $\Delta\varphi$ equal to $\pi/2$. FIG. 5 is a graph of an experimental intensity signal recorded by a pixel of charge coupled device when an object is scanned through the in-plane focus of a microscope objective while a pattern of the form described in Eq. (1) is projected onto the object's surface. The object that is scanned is a silicon carbide flat. Similar to FIG. 4, the vertical axis corresponds to light intensity values whereas the horizontal axis represents the time over which the signal is recorded. The phase increment of the pattern projected onto the object's surface in FIG. 5 has a phase increment $\Delta\varphi$ equal to $\pi/2$. The microscope used in the experiment is equipped with a 10× objective with NA=0.21.

As shown in FIGS. 4-5, the light signal intensity of the acquired images is a function of the scan position and includes an amplitude modulation. The scan position that results in the largest amplitude modulation of the light intensity signal corresponds to the position where the object's surface intersects the focal plane, i.e., the position of best focus. By identifying the position of best focus at multiple locations across the surface of the object, the relative height of the locations can be measured and, in some implementations, an image of the object's surface can be reconstructed.

Each light intensity signal emulates or has characteristics similar to a typical scanning white light interference (SWLI) signal, where a localized signal envelope 400 is modulated by a quasi-constant-frequency carrier 402. The frequency of the carrier 402 is independent of the attributes (e.g., numerical aperture, wavelength, etc.) of the optical system used to image the object and is instead determined by the phase increment $\Delta\phi$ of the pattern projected onto the object's surface. In contrast to a SWLI signal, however, there is no optical path difference that relates to the object's surface height. Instead, as explained above, an object's surface height is determined based on the relative location of the maximum amplitude of the contrast envelope.

Given the similarities between the recorded light intensity signal and a SWLI signal, processing algorithms developed for processing SWLI data can be used to analyze the light intensity signals and extract surface information about the sample object. In some implementations, the algorithms developed for analyzing SWLI data were designed for a particular carrier frequency or frequency band. Accordingly, light intensity signals obtained using the present method can be readily matched with algorithms designed for SWLI analysis. Examples of applicable SWLI algorithms include frequency domain analysis (FDA) and sliding windows least square (LSQ) fits, among others. In FDA, identifying the scan position of the object includes transforming the light intensity signal into a frequency domain. That is, the light intensity signal at each pixel can be modeled as a collection of single-wavelength fringe patterns superimposed incoherently upon one another, where each fringe pattern has a unique spatial frequency or wave number k, defined as the rate of change of phase with scan position. The peak fringe contrast occurs at a scan position for which the phases of the constituent patterns match. Accordingly, knowledge of the relative phases at any given position can then be directly related to height values on the object's surface.

Figure 6:
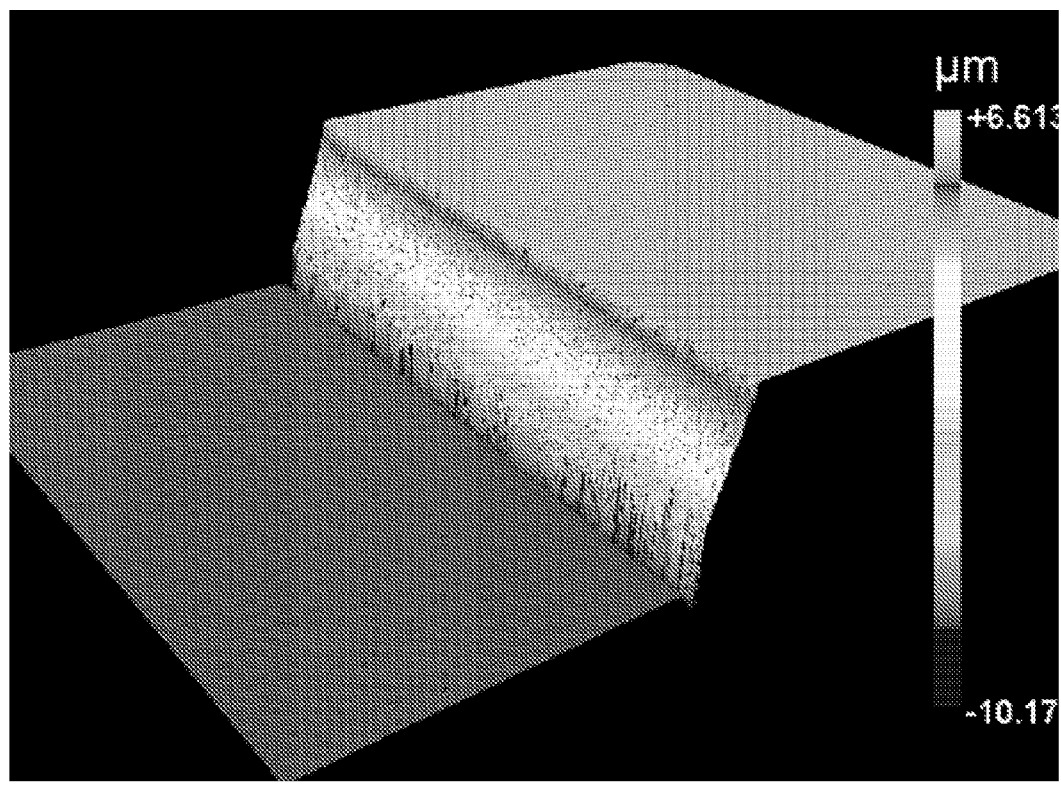
FIG. 6 is an exemplary topography map of a 13-μm step height step generated by FDA processing of light intensity signals.

FIG. 6 is an exemplary topography map of a 13-μm step height standard generated by FDA processing of light intensity signals. The height standard was acquired from VLSI, Inc. The data was acquired using a 100× microscope objective having a NA=0.95. The pattern projected onto the sample object was described using Eq. 1 where the pitch $\Lambda$ was equivalent to the length of 6 linearly arranged pixels of the image-recording device and the phase shift $\Delta\phi$ was equal to $\pi/2$. For the charge-coupled device used in this example, each pixel length was about 7.4 μm.

In LSQ, a fitting function based on a model of the expected signal is applied to the light intensity signal imaged at each pixel. The fitting function includes one or more variable parameters that, at a given scan position, are varied to optimize the fit to the actual signal by means of, for example, a least-squares optimization (although other optimizations techniques may be used). Next, the pattern matching technique performs a fit sequentially through the scan by means of a least-squares optimization (although other optimizations techniques may be used). The scan position for which the LSQ fit is most successful locates the signal, and the maximum value of the fit corresponds to the location of the position of best-focus. A more detailed discussion of using FDA or LSQ to extract surface topography can be found in U.S. Pat. No. 5,398,113 and U.S. Pat. No. 7,321,431, respectively, both of which are incorporated herein by reference.

Other data analysis methods also can be used to extract topography information. For example, in some implementations, the light intensity signal amplitude is computed using a sliding phase-shifting algorithm. The location at which the maximum amplitude occurs then corresponds to the position of best-focus. In some implementations, a model fit function can be applied to selected amplitude data points in the neighborhood of the maximum experimental amplitude location in order to identify the location of best-focus. The model function can include, for example, a parabola, Gaussian, or Lorentzian fit. Other model functions may be applied as well.

An example form of sliding phase-shifting algorithm is given below where four successive intensity values I are obtained as the sample is scanned. The intensity values then are combined to provide an estimate of the local signal modulation V.

$$I_1 = 1 + V(Z)\cos\left(2\pi\frac{x}{\Lambda}\right) \quad (3)$$

$$I_2 = 1 + V(Z+dZ)\cos\left(2\pi\frac{x}{\Lambda} + \frac{\pi}{2}\right)$$

$$I_3 = 1 + V(Z+2dZ)\cos\left(2\pi\frac{x}{\Lambda} + \pi\right)$$

$$I_4 = 1 + V(Z+3dZ)\cos\left(2\pi\frac{x}{\Lambda} + \frac{3\pi}{2}\right)$$

$$V\left(Z+\frac{3}{2}dZ\right) = \sqrt{(I_1-I_3)^2 + (I_2-I_4)^2}$$

where dZ is the scan increment between successive acquisitions within the measurement volume, x is the position of a pixel in the field of view and $\Lambda$ is the pitch of the projected pattern. The phase-shift is $\pi/2$ in this example.

In some embodiments, other algorithms having a larger number of frames and offering better noise rejection capability can be used. However, such algorithms can require approximating the envelope as constant over a larger Z-range. For example, five successive intensity samples yield the following estimate of modulation:

$$V(Z+2dZ) = \sqrt{(2I_3-I_1-I_5)^2 + 4(I_2-I_4)^2} \quad (4)$$

Alternatively, the signal associate with each individual pixel can be with a model function that has the form of an envelope multiplied by a sinusoidal carrier. For example, a model intensity function can be renresented as:

$$I(i) = A + B\exp\left(-\frac{(i-i_0)^2}{2\sigma^2}\right)\cos\left(i\frac{\pi}{2} + \psi\right) \quad (5)$$

where i is the index of the measured intensity during the scan, A, B, $i_0$ and $\psi$ are fit parameters, determined for instance using an iterative least-squares procedure (see Levenberg-Marquardt algorithm, "Numerical recipes in C," Cambridge University Press, incorporated herein by reference in its entirety).

Figure 7:
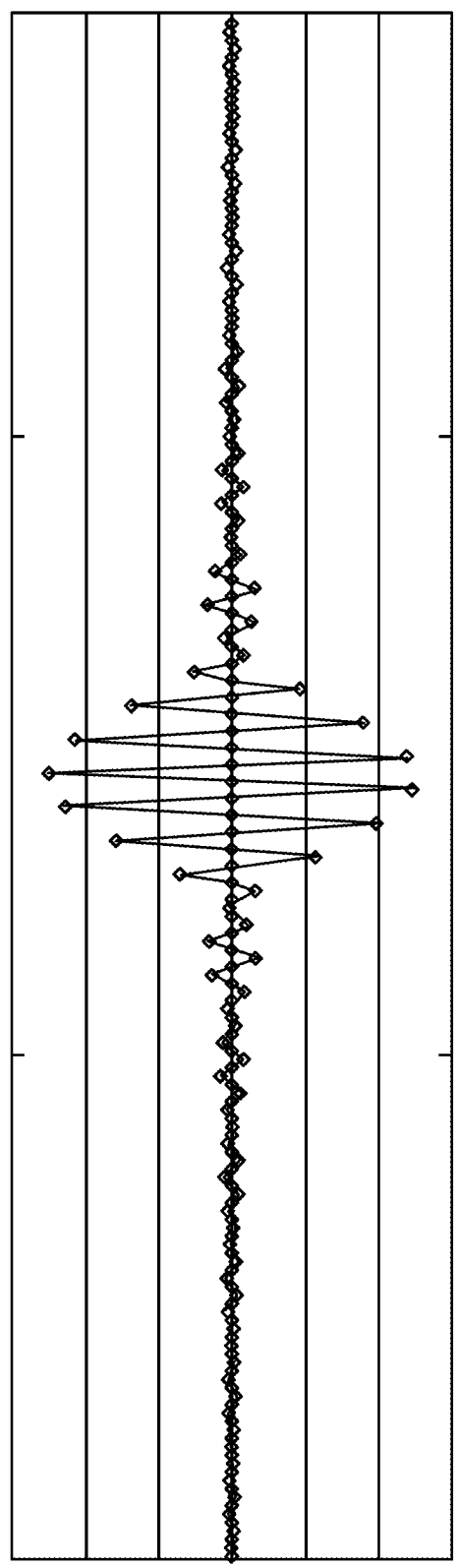
FIG. 7 is a graph of a simulated intensity signal.

In some embodiments, controlling the width of the modulated signal envelope can change the measurement speed and/or resolution. Light intensity signals having increasingly compact contrast envelopes enable, in some implementations, form measurements capable of correspondingly higher vertical resolution (i.e. resolution along the direction of the scan). A form measurement is a metrology application where the goal is to measure the departure of an object surface from its intended form (as a result of a manufacturing process) or to obtain a topography map of an unknown object surface. The width of the modulated signal envelope can be controlled, for example, by adjusting the pitch $\Lambda$ of the pattern projected onto the object's surface. FIG. 7 is a graph of a simulated intensity signal as would be observed by an individual pixel of an image-recording device when a pattern having half the pitch (i.e., twice the frequency) of the pattern used in FIG. 4 is projected onto an object's surface as the object is translated through an in-plane focus of a microscope objective. As shown in the graph of FIG. 7, the width of the modulated signal envelope has decreased relative to the width of the signal envelope shown in the graph of FIG. 4. The highest vertical resolution is obtainable when the frequency of the projected pattern in object space is chosen to be half of the cut-off frequency $(2NA)/\lambda$ of the optical system.

Conversely, a broader envelope can decrease the potential resolution of the system (i.e., by increasing the distance traveled by the sample object between frames of data captured by the image-recording device) but also enable an increase in scan speed. Such increases in scan speed can be advantageous for production/manufacturing floor applications that require examining the surface of a sample object quickly. Alternatively, or in addition, the increased speed can be advantageous in certain implementations for applications requiring autofocus or autofocus and automatic orientation (e.g., tip/tilt) corrections.

An example application requiring autofocus is in white-light interference microscopy. In this procedure, the scanning step size is chosen to be an integer multiple of the effective mean wavelength of the system such that the interference fringes produced by the interferometer are washed out during the fast focus scan where structured illumination is used. For SWLI measurements the structured illumination pattern is replaced by a static uniform or tailored pattern.

In some embodiments, the scan speed can be improved further by altering the phase shift of the pattern projected onto the surface of the sample object. For example, if the phase shift $\Delta\phi$ is set equal to $\pi$, the difference of the intensity value between a first frame of image data captured by the image-recording device and a subsequent frame of image data captured by the image-recording device corresponds to a direct estimate of the signal envelope magnitude. As a result, the computational complexity of analyzing the image data is reduced, resulting in increased computation speed. In some implementations, however, patterns that have a phase shift $\Delta\phi$ set equal to it are less suitable for topography measurements because one or more pixels may exhibit low or no signal modulation at every position of the scan. In some implementations, signals captured by the image-recording device that exhibit low signal modulation can be discarded without further analysis.

In some embodiments, additional zero values are inserted between each measured signal value captured by the image-recording device prior to processing the signal using FDA. An example using FDA in this manner is illustrated with respect to FIGS. 8A-8C. Each of FIGS. 8A-8C is a plot of a simulated analog intensity signal (solid line) overlaid with a corresponding digitized version (dashed line with diamond shaped markers) of the intensity signal. In particular, the diamond-shaped markers in the plot correspond to digitized values of the simulated intensity signal. That is to say, the markers are representative of intensity values as would be recorded at a single pixel location of an image-recording device, were a physical scan of a sample performed. The phase-shift between successive illumination patterns for signal illustrated in FIG. 8A is $\pi/2$. FIG. 8B shows a similar simulated intensity signal where the scan speed is doubled and the phase-shift between successive illumination patterns is increased to $\pi$. In contrast to the signal shown in FIG. 8A, the signal illustrated in FIG. 8B is sampled at the Nyquist frequency. In some implementations, sampling at this frequency can be undesirable for frequency domain analysis due to a loss of signal modulation.

To effectively sample the signal shown in FIG. 8B at the same rate as the signal sampled in FIG. 8A, zero values are inserted between the measured intensity values. A plot of the resulting sampled signal overlaid with the analog signal is illustrated in FIG. 8C. It should be noted that in practice, the inserted value would correspond to the local mean as opposed to a zero value.

Figure 9A:
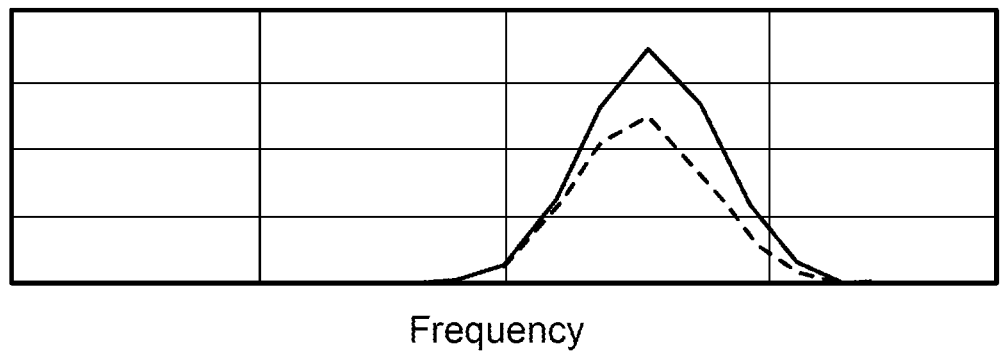
FIG. 9A is a plot of the magnitude of the digitized sample signal from FIG. 8A and the phase of the digitized intensity signal from FIG. 8C.
Figure 9B:
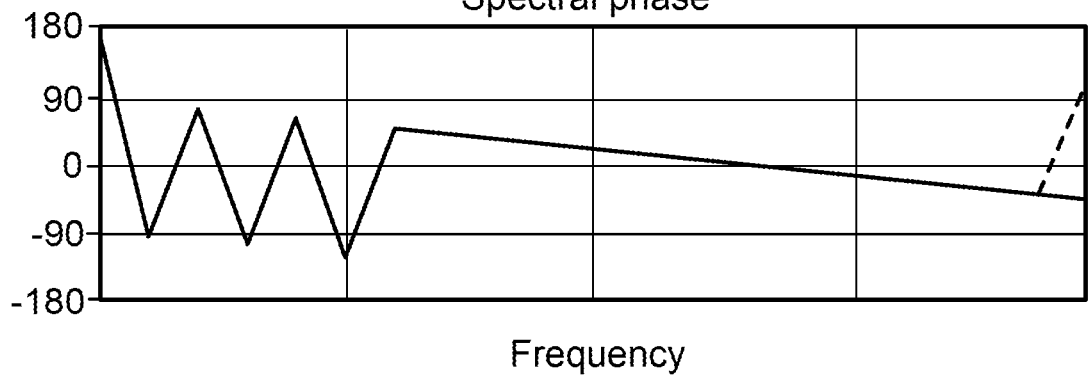
FIG. 9B is a plot of the phase of the digitized sample signal from FIG. 8A and the magnitude of the digitized intensity signal from FIG. 8C.

FIGS. 9A and 9B compare the magnitude and phase, respectively, of the spectrum of the digitized sample signal from FIG. 8C (dashed line) and the digitized sample signal from FIG. 8A (solid line). The magnitude and phase are obtained by Fourier transformation of the corresponding digitized sample. As shown in FIG. 9A, the phase information is identical in the spectra for the recorded sample from FIG. 8A and for zero-padded signal from FIG. 8C. Accordingly, computation of sample position from the phase slope would yield the same result under either analysis, thus allowing an increase in sampling frequency without a loss in position information.

It should be noted, however, that in some implementations, the illumination pattern phase induces a reduction in the signal magnitude recorded by the pixel location. That is, the sampled values may not reflect the true magnitude of the illumination pattern reflected to the image-recording device. For example, FIG. 10A is a plot of a simulated analog intensity signal (solid line) overlaid with a corresponding digitized sampling (dashed line with diamond shaped markers) of the simulated signal, where the phase shift of the illumination pattern is $\pi$. As shown in the example of FIG. 10A, the magnitude of the digitized sample signal is substantially less than the corresponding simulated analog signal. FIG. 10B is a plot illustrating the same simulated analog intensity signal and digitized sample signal of FIG. 10A, where zero values have been inserted into the digitized sample signal. The relative reduction in signal magnitude of the digitized sample signal can lead to a lower signal-to-noise ratio for the particular pixel at which the signal is recorded. Thus, although doubling scan-speed enables rapidly locating the focus position of a sample (as well as rapidly measuring the tip and tilt of a surface), topography information may be degraded.

Programmable Patterns

In some implementations, a programmable SLM can be used to optimize the imaging system based on the particular application or sample object being measured. For example, as explained above, modifying the pitch of the pattern projected onto a surface of a sample object allows adjustment of the resolution and/or speed with which data is obtained. Coarser pattern features (i.e., higher pattern pitch/lower pattern frequency) enable, in some cases, improved robustness when analyzing rough objects. That is to say, the system is less susceptible to variations in height due to surface roughness. In some cases, coarser pattern features enable the system to increase the range over which measurements can be obtained, thus allowing measurements of features having high-slopes, e.g., on specular objects. In some implementations, employing patterns with coarser features enables an increase in scan speed, where the increased speed is due to a broadened contrast envelope having larger z-sampling steps. In contrast, finer pattern features (i.e., lower pattern pitch/higher pattern frequency) can, in some implementations, offer advantages such as providing increased height profiling resolution, especially for optically smooth objects.

In some embodiments, a programmable SLM can be used to adjust the illumination pattern based on the characteristics of the optical system. For example, when using a microscope platform that accommodates a wide variety of objectives (e.g., having magnifications ranging from 4× to 100×), the illumination pattern frequency can be adjusted based on the numerical aperture and focal length of the particular objective in use so that the pattern can be properly resolved. In an exemplary implementation, a system is configured such that the maximum contrast of a pattern projected on a given sample is the same regardless of the magnification, in order to maintain a desired signal to noise ratio. In particular, the illumination pattern is projected with a constant normalized frequency with respect to the cut-off frequency $\lambda/(2NA)$ of the optical system. In order to obtain the constant normalized frequency, the product of the pattern's pitch on the SLM with the objective's pupil size is set to be a constant. For example, when switching from a first objective to a second objective having a smaller pupil, the pitch of the pattern on the SLM is increased to maintain the desired pattern contrast.

In some embodiments, a programmable SLM can be used to adjust both the frequency and orientation of the intensity modulation applied to the illumination pattern. The ability to alter the illumination pattern orientation can be useful for analyzing the topography of object surfaces having smoothly varying and/or high sloping features along more than one direction. For example, when performing measurements of features having smoothly curved surfaces (e.g., microlenses, micro-retroreflectors, patterned diffusing optics for LCD display backlighting), the level of topography information recovered can be improved when the illumination pattern modulation direction is aligned to be substantially perpendicular to the surface gradient direction of the curved feature. Accordingly, the SLM can be programmed to rotate, translate or alter an illumination pattern's direction of intensity modulation depending on the slope of the feature to be analyzed.

If the surface gradient direction of a feature on an object's surface varies in multiple directions (e.g., microlenses, micro-retroreflectors), it can be advantageous, in some implementations, to illuminate the object's surface with multiple patterns, each pattern having a modulation direction substantially perpendicular to a different surface gradient direction of the feature. Alternatively, or in addition, the object can be illuminated with a single complex pattern modulated over multiple different directions.

Figure 11:
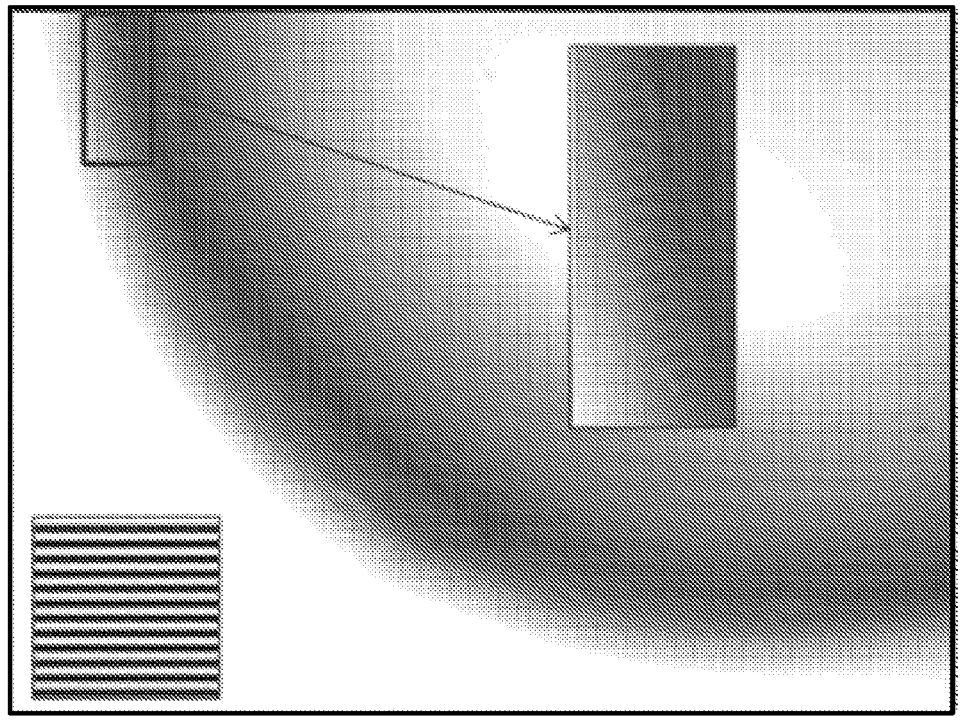
FIGS. 11-13 are exemplary images of a microlens onto which an illumination pattern is projected.
Figure 12:
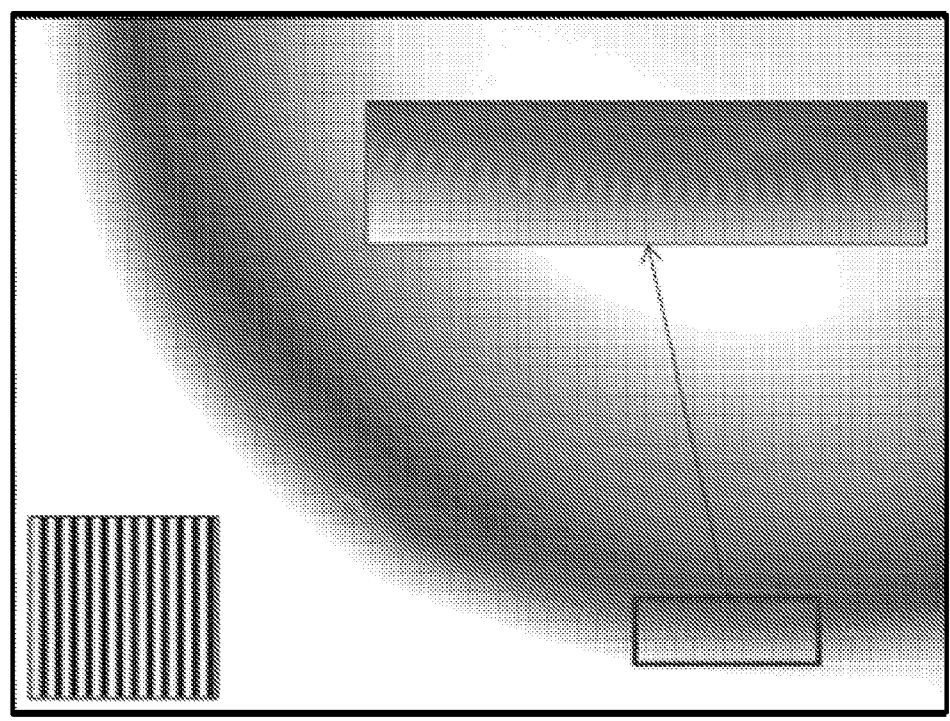

FIGS. 11 and 12 each show an exemplary image of a microlens onto which a one-dimensional illumination pattern is projected. The microlens in each image is formed from a polymer material and is positioned on a glass substrate. The illumination pattern projected onto the microlens in FIG. 11 is sinusoidal with horizontal fringes, as shown in the inset at the bottom left of FIG. 11. Similarly, the illumination pattern projected onto the microlens in FIG. 12 is sinusoidal, although with vertical fringes, as shown in the corresponding inset at the bottom left of FIG. 12. The one-dimensional patterns do not, however, provide information everywhere along the high-slope portions of the microlens. Instead, as shown in FIG. 11, a modulating pattern is observable at the foot of the left side of the microlens (see enlarged region) but not at the bottom side of the microlens. Similarly, FIG. 12 shows that a modulating pattern is observable at the foot of the bottom side of the microlens (see enlarged region) but not at the left side of the microlens.

Figure 13:
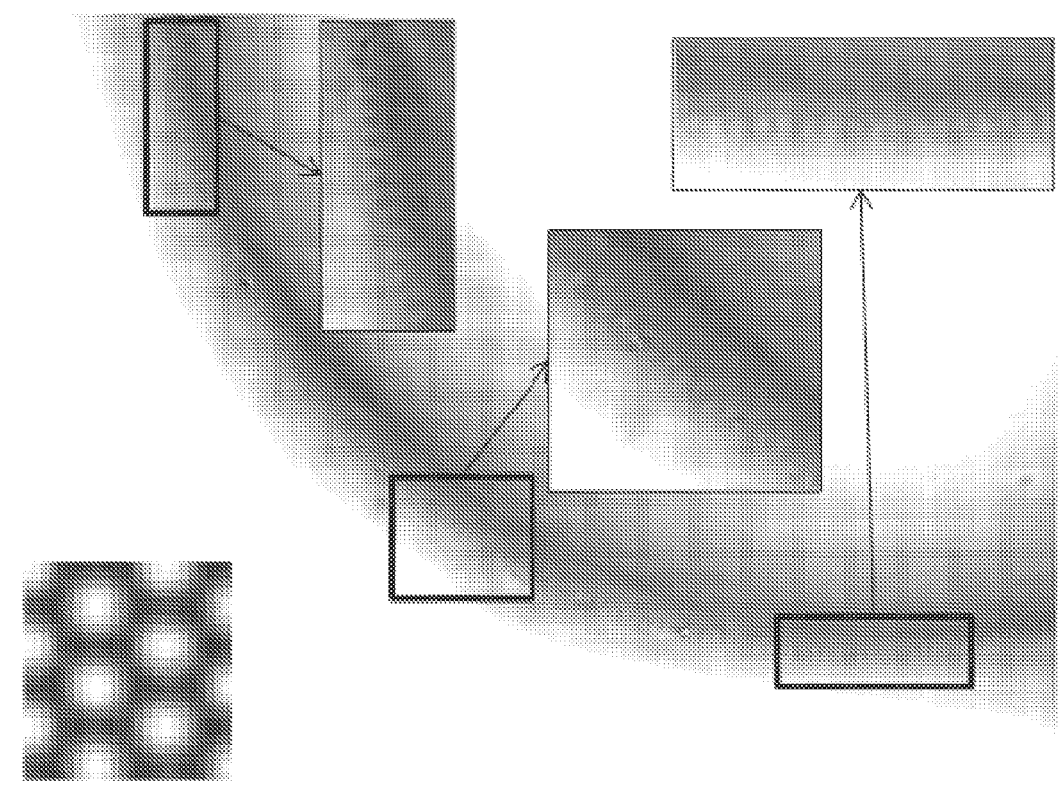

To compensate for the lack of modulation information provided by one-dimensional patterns, a more complex pattern or patterns can be used. For example, in some cases, the illumination pattern projected onto a surface of an object can include a composition of two or more different illumination patterns. FIG. 13 shows an exemplary image of a microlens onto which a complex illumination pattern, composed of three rotated one-dimensional sinusoidal patterns, is projected. A portion of the complex illumination pattern is shown in the inset at the bottom left of FIG. 13. In this example, a modulation pattern is now observable everywhere along the foot of the microlens. Accordingly, topographical information can be obtained around the entire perimeter of the object.

Alternatively, or in addition, two or more individual illumination patterns can be projected sequentially onto a surface of an object. For example, in some implementations, topographical information about the surface of an object can be obtained by performing three (or more) separate scans of the object surface. For each scan, the illumination pattern can be altered with respect to the orientation of the illumination patterns for the other two scans. For example, the orientation pattern can be translated, rotated, skewed, or stretched, among other alterations. In some implementations, an entirely different illumination pattern can be used for each separate scan instead of altering the orientation of a single scan. Although the three separate scans may increase total measurement time, the noise of the measurement can be improved due to the larger amount of information that is collected. In addition, the application of one-dimensional patterns, as opposed to two-dimensional patterns can, in some cases, result in modulation patterns having higher contrast at the plane of best-focus. The three separate data sets of data then are merged to obtain topographical information about the object surface. In some implementations, data corresponding to the same region of the object that is valid in at least two separate scans can be used to adjust tip, tilt, or piston between separate datasets.

In some implementations, it is also possible to compensate for reflectivity variations across the surface of a sample object by modifying the illumination pattern projected onto the object. For example, in some cases, objects having both high and low surface gradients (such as the microlens in each of FIGS. 11-13) appear darker in the high slope regions, as a result of less reflected light being captured by the optical components used to image the illumination pattern (imaging optics), and brighter in the low slope regions where much of the reflected light is captured by the imaging optics. The relative reflectivity of a feature on an object's surface can be measured based on the magnitude of a light intensity signal captured at a corresponding pixel of an image-recording device. To compensate for the variation in reflectivity, an iterative scan can be implemented where reflectivity data from a first scan in the iteration is used to subsequently adjust an intensity distribution across the illumination pattern projected onto the object's surface in a subsequent scan. For example, if a first scan of a sample object results in an apparent object reflectivity variation that follows a function $r(x, y)$, then a modified projected illumination pattern for a subsequent scan can be computed according to:

$$P(x, y, n) = \left(1 + \cos\left(\frac{2\pi}{\Lambda}x + n\Delta\varphi\right)\right)\frac{\min(r(x, y)) + \varepsilon}{r(x, y) + \varepsilon} \quad (6)$$

where the quantity $\varepsilon$ is used to prevent division by zero and to control the dynamic range of the pattern according to the resolution of the SLM.

Alternatively, or in addition, it is possible to use the non-contact surface characterization methods and systems provided in this disclosure to measure the absorption of a sample surface. For example, when analyzing objects where one expects the surface texture to result in uniform scattering losses, the light absorption can be computed based on the difference between the amount of light used to illuminate the object and the amount of reflected light captured by the image-recording device at the plane of best focus.

Optical Configurations

A wide variety of optical imaging configurations can be implemented for use in structured illumination measurement applications. In some instances, the optical configuration can be arranged to image samples having a non-planar surface on the macro-scale. For example, to measure the deviation of a curved sample surface from an ideal spherical surface, the sample can be imaged using one or more optics that map the detector plane of the image-recording device onto the spherical best-focus surface in object space. In some implementations, more complex geometries of the measurement surface can be achieved using standard optical system design and manufacturing tools. In general, an optical configuration having a large number of reflective, refractive and/or diffractive elements enables imaging of a measurement surface that departs substantially from a sphere or a plane.

Figure 14:
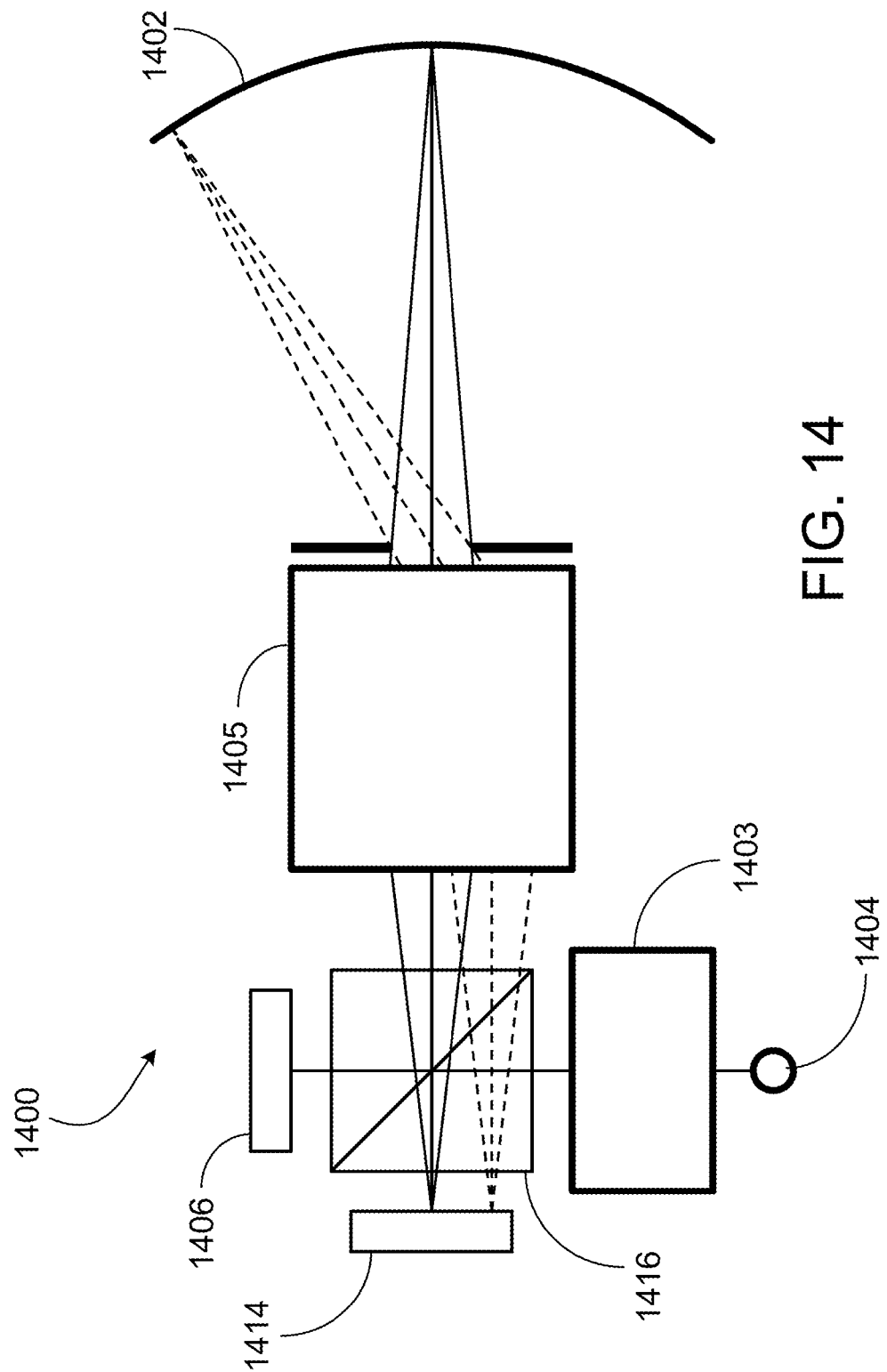
FIG. 14 is a schematic diagram of an exemplary structured illumination imaging system.

FIG. 14 is a schematic diagram of an exemplary structured illumination imaging system 1400 configured to image a sample 1402 having a curved surface on the macro scale. As shown in the example, image-recording device 1414 and SLM 1406 are located at a common distance from imaging optics 1405. The illumination optics 1403 are used to illuminate the sample 1402 using light from source 1404 and imaging optics 1405 are used to capture light reflected from sample 1402. In some implementations, the illumination optics 1403 include a polarizer (not shown) and the imaging optics 1405 include a quarterwave plate (not shown) to send light reflected from the object onto detector 1414. A polarizing beamsplitter 1416 prevents polarized illumination light from reaching the detector plane of the image-recording device 1414. The SLM 1406 generates an illumination pattern that is projected in object space in the vicinity of a curved surface, which is conjugate with the detector plane. A maximum pattern contrast then is observed for object points of a part of the sample 1402 to be characterized that lie on this curved surface. As in previous examples, the coordinate system is defined such that the z-axis is parallel to the optical axis of an objective lens (not shown) and the x and y-axes are parallel to the lens' plane of best-focus such that xyz forms an orthogonal coordinate system.

Acquisition of data as the sample 1402 is scanned through the position of best-focus can be performed in one of several alternative ways. In a first implementation, a surface of the sample 1402 is scanned longitudinally along the z-axis with respect to the entire optical system 1400. In another implementation, the imaging optics and the object are collectively scanned longitudinally as a unit with respect to the other components of the system (e.g., source 1404, beamsplitter 1416, SLM 1406, image-recording device 1414 and illumination optics 1403), thus preserving the mapping of detector pixels onto fixed locations of the sample surface. In some implementations, the motion of one or more of the imaging optics and/or the sample surface can be independently controlled.

Figure 15:
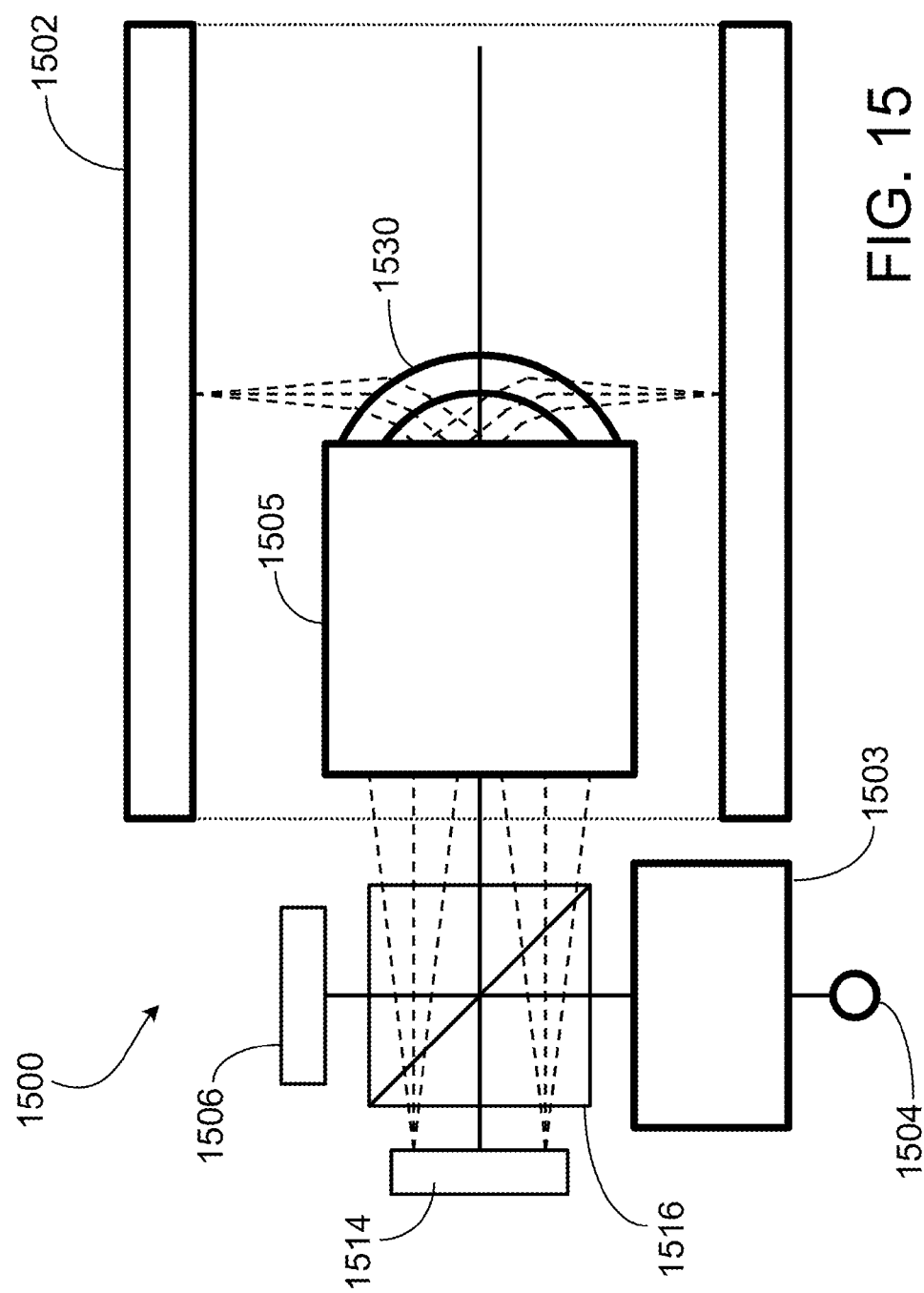
FIG. 15 is a schematic diagram of an exemplary imaging system.

In some embodiments, off-the-shelf or custom-designed optical components can be incorporated into a structured illumination imaging system to provide flexibility in the type of imaging surface that can be achieved. For example, in some implementations, a fisheye lens can be used to characterize the inside of cylindrical objects. FIG. 15 is a schematic diagram of an exemplary imaging system 1500 configured to image a sample 1502 having a cylindrical opening in the shape of a bore, in which the imaging optics 1505 include a fisheye lens 1530. In this example, an inner surface of the bore 1502 is acquired while the imaging optics 1505 are held stationary with respect to the cylinder bore and other portions of the imaging system (e.g., source 1504, image-recording device 1514, illumination optics 1503, SLM 1506, and/or beamsplitter 1516, among others) scan along the cylinder central axis (i.e., the z-direction).

Figure 16:
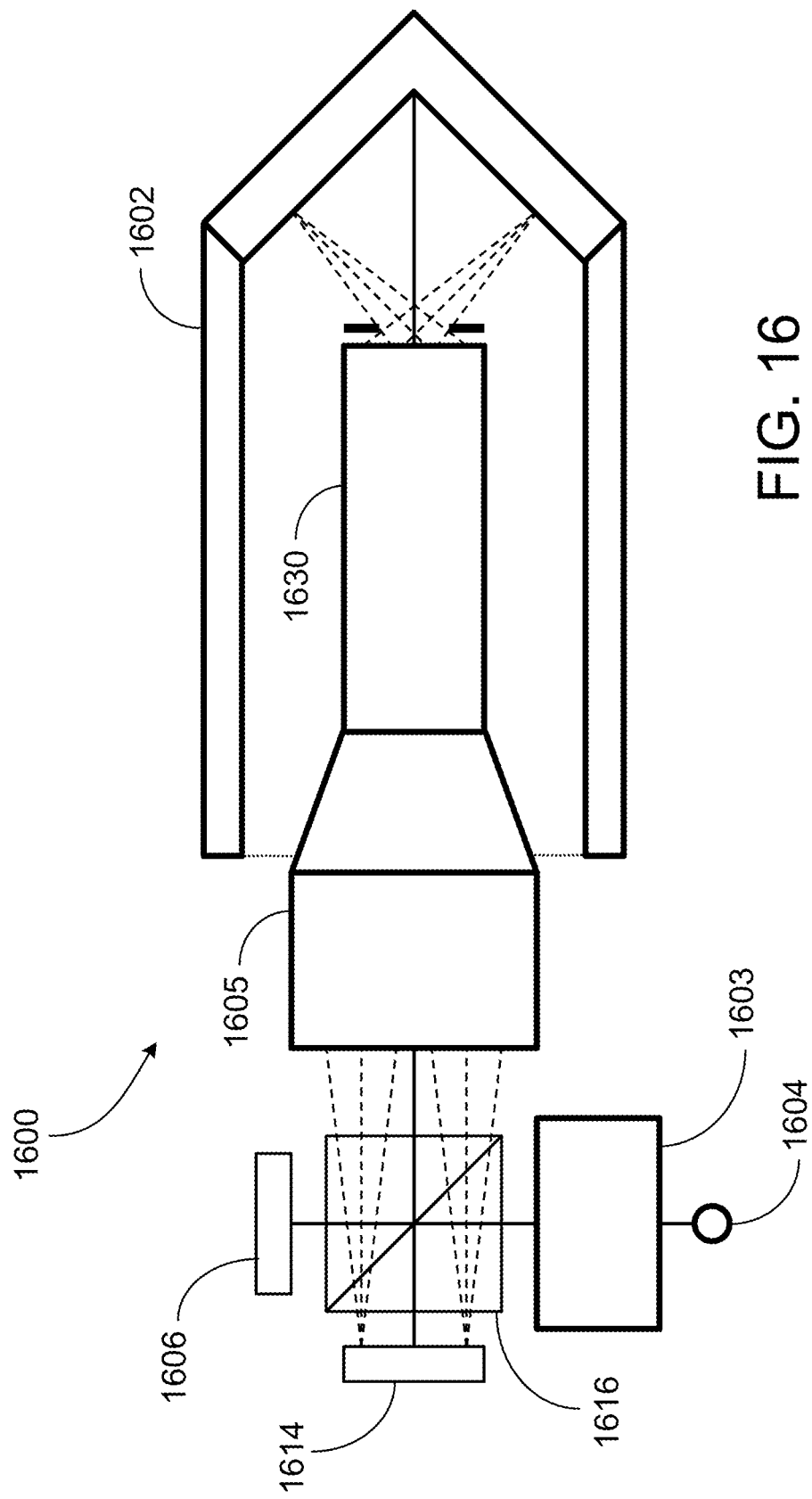
FIG. 16 is a schematic diagram of an exemplary imaging system.

Other optical components can be incorporated into a structured illumination imaging system. For example, in some implementations, endoscopes enable wide-field imaging of the inside of small volumes, such as machined components or biological objects. FIG. 16 is a schematic diagram of an exemplary structured illumination imaging system 1600 that includes an endoscope 1630 used for imaging the inside of a conical valve seat 1602. The imaging optics 1605 are fixed with respect to the valve seat 1602, while other portions of the imaging system (e.g., source 1604, image-recording device 1614, illumination optics 1603, SLM 1606, and/or beamsplitter 1616, among others) scan along the valve seat central axis (i.e., the z-direction), thus enabling imaging of the conical interior of the valve seat.

In some implementations, zoom lenses can be used to change how ray directions in object space are mapped onto a detector plane of the image-recording device. FIGS. 17A and 17B each are schematic diagrams of an exemplary structured illumination imaging system 1700, in which the imaging optics 1705 includes a zoom lens 1730 Other components of the system 1700 include source 1704, image-recording device 1714, beamsplitter 1716, illumination optics 1703 and SLM 1706. As shown in FIG. 17A, when the focal length of the zoom lens 1730 is long, the angular range over which the lens 1730 can image a surface is small, as represented by the curvature of sample 1702. In contrast, when the focal length of the zoom lens 1730 is short, the angular range over which the lens can image a surface is larger, as represented by the curvature of sample 1722 in FIG. 17B. Thus, by adjusting the focal length of the zoom lens 1730, the measurement range of the system 1700 can be modified. In addition, curved surfaces having different nominal radius of curvature can be imaged.

In some embodiments, the capability to image surfaces of varying curvature can be advantageously used for piece-wise profiling of aspheric surfaces. For example, FIGS. 18A and 18B illustrate schematic diagrams of an exemplary structured illumination system 1800 used to image samples having aspheric surfaces. Components of the system 1800 include source 1804, image-recording device 1814, beamsplitter 1816, illumination optics 1803 and SLM 1806. Similar to examples shown in FIGS. 17A and 17B, the imaging optics 1805 include a zoom lens 1830. When the focal length of the zoom lens 1830 is set to be relatively long, the system 1800 can image the low curvature portions of the aspheric surface of sample 1802. In contrast, when the focal length of the zoom lens 1830 is set to be relatively short, the higher curvature regions of the aspheric sample 1802 can be imaged.

Exemplary Applications

3D Imaging

The non-contact surface characterization methods and systems described above can be used to provide information about topography and surface texture of an object such as height, reflectivity, or absorption, among other features. In some embodiments, a reflectivity of the sample can be measured in at least two color channels such that color information can be presented alongside or merged with the topography data to create a 3D image of the object. Color reflectivity can be derived, for example, based on a light intensity signal captured at each pixel of an image-recording device, where the signal is reflected off of an object located at the position of best-focus for a particular object lens. Alternatively, color reflectivity can be derived from the mean light intensity signal measured at the position of best-focus for a particular objective lens. Devices which can be used to determine color reflectivity information include image-recording devices having multiple color channels and detectors (e.g., 3-CCD cameras) or image-recording devices that implement spatial color filters (e.g., a single CCD with a Bayer filter).

The illumination pattern can be projected using a broadband light source that emits light in the visible spectrum for the purpose of monitoring color. For example, the illumination source can include, but is not limited to, a white-light LED, an array of monochromatic LEDs, where each LED emits light of a different wavelength in the visible spectrum, a halogen lamp, an arc lamp, a supercontinuum laser, or a discharge lamp, among others.

Figure 19B:
FIG. 19B is a color image of the surface of the sample object of FIG. 19A.
Figure 19A:
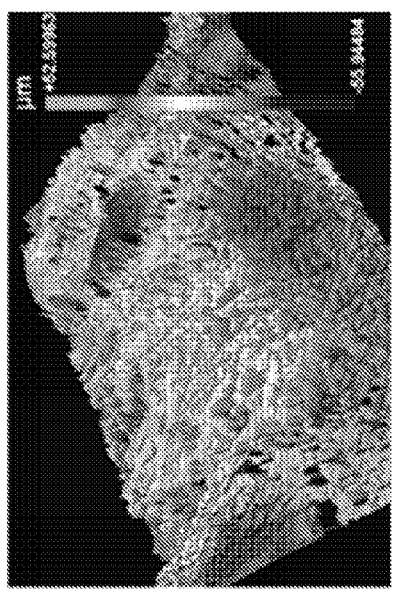
FIG. 19A is a 3D graph of experimental topography data collected on a sample object.
Figure 19C:
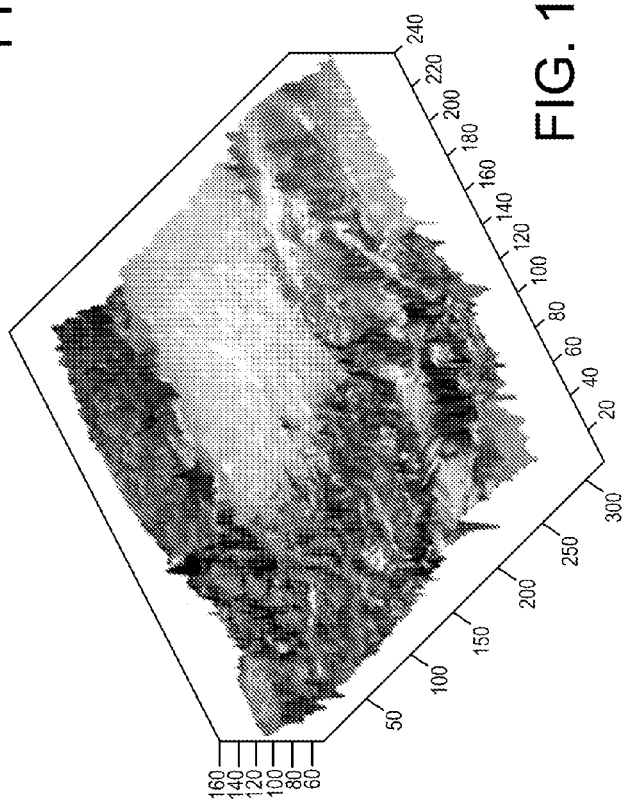
FIG. 19C is an exemplary color image produced by combining the topographical data of FIG. 19A with the color image of FIG. 19B.

FIG. 19A is a 3D graph of experimental topography data collected on a sample object using the non-contact surface characterization method described above. The sample object is a business card having 1) ridges created by the printing of black and red inks on the surface of the card, and 2) an indentation resulting from drawing on the card with a blue pen. FIG. 19B is a color image of the surface of the sample object of FIG. 19A obtained using the same color camera to obtain the topography information shown in FIG. 19A. FIG. 19C is an exemplary color image produced by combining the topographical data of FIG. 19A with the color image of FIG. 19B. The image shown in FIG. 19C offers a natural visualization of the 3D shape, texture and color of the measured surface of the sample object.

Film Thickness

The non-contact surface characterization methods and systems of the present disclosure also can be used to determine film thickness information of a sample object when the sample object being measured includes multiple interfaces between transparent materials. To determine the thickness of each film, the light intensity signal captured by the image-recording device is decomposed into separate light intensity signals for each corresponding interface in the sample object. Examples of LSQ methods for determining the separate light intensity signals are disclosed in U.S. Pat. No. 7,321,431. The minimum resolvable film thickness is a function of the width of the modulated contrast envelope produced by the scan procedure. In addition, objective lenses having higher NA are capable of measuring thinner films than objective lenses having a lower NA.

Positioning of Optics in Laser Eye Surgery

In some implementations, the non-characterization methods and systems described in the present disclosure can be used to identify and adjust the position of optics in laser eye surgery. For example, in certain laser eye surgery applications, a laser (e.g., a femtosecond laser) can be used to cut a flap of controlled thickness in a cornea. Prior to cutting the flap, a glass plate comes into contact with the cornea to allow the eye surgeon to determine how thick to make the cut. The depth of the cut depends, in part, on knowledge of the position of the glass plate with respect to a plane of best focus of the laser optics. By utilizing the non-contact surface characterization technique of the present disclosure, it is possible, in some implementations to provide methods and systems for quickly identifying whether the glass plate is in proper position for the desired incision depth.

FIG. 20 is a schematic of an exemplary system 2000 for determining whether a glass plate is in position for performing the foregoing laser eye surgery. The system 2000 includes optics similar to those shown in FIGS. 1 and 2. In the present system 2000, however, laser optics 2018 function as the objective lens. A tube lens 2020 re-images the field of the laser optics 2018 onto an image-recording device 2014. An illumination portion 2003 includes a light modulator 2006 that modulates a light intensity pattern projected onto a plane of best-focus of the laser optics 2018. A glass plate 2002 for determining the depth of an incision into a cornea 2040 is scanned through the plane of best-focus. When the glass plate 2002 deviates from the position of best-focus during the scan, the image of the modulated pattern obtained by the image-recording device 2014 exhibits blurring and a reduction in contrast.

During the scan of the glass plate 2002, the projected light intensity pattern is shifted laterally to create a periodic temporal light intensity signal at each pixel of the image-recording device 2014. Each light intensity signal has a characteristic modulation envelope that peaks in magnitude when a surface of the glass plate 2002 imaged by the pixel is translated into the scan position corresponding to plane of best-focus. One or more algorithms (e.g., FDA, LSQ) then can be used to determine the peak envelope location and thus the position of the glass plate 2002. The glass plate 2002 then can be translated into the desired position as needed for performing the incision into the cornea 2040.

Advantages of using the foregoing system in laser eye surgery applications can include, for example, the ability to directly position an optical interface (e.g., the glass plate) with respect to a focal plane of the laser optics without requiring intermediate datum. In some cases, the components used to implement the technique (e.g., spatial light modulator) can be implemented into existing systems for laser eye surgery applications without significant or substantial modifications. In some implementations, the measurement of the bottom air-glass interface of the glass plate (i.e., the interface of the plate closest to the cornea) is not affected by the presence of the top interface of the glass plate (i.e., the interface of the plate furthest from the cornea). Additionally, in some cases, the system allows for quick auto-focus of the optics used to determine the incision depth. In some implementations, the foregoing technique allows measurement of plate tilt, flatness or field curvature of the laser optics.

A number of implementations of the invention have been described. Nevertheless, it will be understood that various modifications may be made without departing from the spirit and scope of the invention. Other embodiments are within the scope of the following claims.

What is claimed is:

1. A method for forming a three-dimensional image of a test object, the method comprising:
directing light to a surface of best-focus of an imaging optic, where the light has an intensity modulation in at least one direction in the surface of best-focus;

scanning a test object relative to the imaging optic so that a surface of the measurement object passes through the surface of best-focus of the imaging optic as the test object is scanned;

for each of a series of positions of the test object during the scan, acquiring a single image of the measurement object using the imaging optic, wherein the intensity modulation of the light in the surface of best-focus is different for successive images;

and forming a three-dimensional image of the test object based on the acquired images.

2. The method of claim 1, wherein the intensity modulation is a two-dimensional intensity modulation.

3. The method of claim 1, wherein the scan positions are evenly spaced.

4. The method of claim 1, wherein the intensity modulation is selected based on a slope of the test object surface.

5. The method of claim 1, wherein the test object is a lens element.

6. The method of claim 1, wherein the three-dimensional image is a monochrome image.

7. The method of claim 1, wherein the three-dimensional image is a color image.

8. The method of claim 1, wherein directing the light to the surface of best-focus comprises imaging a spatial light modulator (SLM) to the surface of best-focus.

9. The method of claim 1, wherein forming the three-dimensional image comprises identifying, for multiple different locations of the test object surface, the scan position corresponding to where each location intersects the surface of best-focus.

10. The method of claim 1, wherein directing the light to the surface of best-focus comprises imaging a pattern-generating plane onto a surface in object space.

11. The method of claim 1, wherein forming the three-dimensional image comprises deriving an intensity signal for each of multiple different locations of the test object surface, each intensity signal corresponding to the intensity of the acquired images at the corresponding location as a function of scan position.

12. The method of claim 1, wherein the intensity modulation is a periodic modulation.

13. The method of claim 8, wherein the intensity modulation of the light in the surface of best-focus is varied using the spatial light modulator.

14. The method of claim 9, wherein an intensity of the acquired images as a function of scan position at each of the different locations includes an amplitude modulation, and identifying the scan position corresponding to where each location intersects the surface of best-focus comprises identifying the scan position where a modulation amplitude is largest.

15. The method of claim 10, wherein the surface is conformal to a shape of the test object.

16. The method of claim 10, wherein the shape of the test object is planar, spherical, parabolic, cylindrical, conical, or aspheric.

17. The method of claim 11, wherein forming the three-dimensional image comprises identifying a scan position corresponding to a maximum amplitude of a modulation of the intensity signal for each location.

18. The method of claim 17, wherein identifying the scan position comprises transforming each intensity signal into a frequency domain.

19. The method of claim 12, wherein the periodic modulation is a sinusoidal modulation.

20. The method of claim 12, wherein a phase of the periodic modulation is varied by less than $2\pi$ between each successive image.

21. The method of claim 20, wherein the phase of the periodic modulation is varied by $\pi$ or less between each successive image.

22. The method of claim 20, wherein the phase of the periodic modulation is varied by $\pi/2$ between each successive image.

23. A method for forming a three-dimensional image of a test object, the method comprising:

forming an image of a spatial light modulator at a surface of best-focus of an imaging optic;

scanning a test object relative to the imaging optic so that a surface of the measurement object passes through a surface of best-focus of the imaging optic as the test object is scanned;

for each of a series of positions of the test object during the scan, acquiring a single image of the test object using the imaging optic, wherein the spatial light modulator varies an intensity modulation in the light forming the image so that the modulation of the light at the surface of best-focus is different for successive images; and forming a three-dimensional image of the test object based on the acquired images.

24. A method for forming a three-dimensional image of a test object, the method comprising:

directing light to a surface of best-focus of an imaging optic, where the light has an intensity modulation in at least one direction in the surface of best-focus;

scanning a test object relative to the imaging optic so that a surface of the measurement object passes through a surface of best-focus of the imaging optic as the test object is scanned;

imaging the surface of best-focus to a multi-element detector;

for each of a series of positions of the test object during the scan, acquiring a single intensity measurement at one or more elements of the multi-element, wherein the intensity modulation of the light in the surface of best-focus is different for successive positions of the test object during the scan; and forming a three-dimensional image of the test object based on the acquired intensity measurements.

25. A system for forming a three-dimensional image of a test object, the system comprising:

a microscope including an imaging optic, the imaging optic having a surface of best-focus;

a spatial light modulator;

one or more optical elements arranged to direct light from the spatial light modulator to form an image of the SLM at the surface of best-focus during operation of the system;

a scanning stage arranged to scan the test object relative to the microscope object during operation of the system so that a surface of the test object intersects the surface of best-focus;

a multi-element detector positioned relative to the microscope such that the microscope forms an image of a field at the surface of best-focus on the multi-element detector during operation of the system; and an electronic control module in communication with the scanning stage, the spatial light modulator, and the multi-element detector, wherein during operation, the system causes the multi-element detector to acquire a single image of the test object for each of multiple scan positions of the test object relative to the imaging optic, causes the SLM to variably modulate the intensity of light at the surface of best-focus in at least one direction so that the intensity modulation of the light is different for successive images, and forms a three-dimensional image of the test object based on the acquired images.

26. The system of claim 25, further comprising a light source arranged to direct light to the SLM during operation of the system.

27. The system of claim 25, wherein the SLM is a reflective SLM.

28. The system of claim 25, wherein the SLM is a transmissive SLM.

29. The system of claim 25, wherein the SLM is a liquid crystal panel.

30. The system of claim 25, wherein the SLM comprises a micro-mirror array.

31. The system of claim 25, wherein the imaging optic has a numerical aperture greater than 0.6.

32. The system of claim 25, wherein the imaging optic has a numerical aperture greater than 0.8.

33. The system of claim 25, wherein the imaging optic has a numerical aperture greater than 0.9.

34. The system of claim 25, wherein the imaging optic has a numerical aperture of 0.95.

35. The system of claim 25, further comprising color filters arranged to filter the wavelength of light forming the images at the multi-element detector.

36. The system of claim 25, wherein the one or more optical elements comprises a fisheye lens.

37. The system of claim 25, wherein the one or more optical elements comprises an endoscope.

38. The system of claim 25, wherein the one or more optical elements comprises a zoom lens.

* * * * *

UNITED STATES PATENT AND TRADEMARK OFFICE
CERTIFICATE OF CORRECTION

PATENT NO.        : 8,649,024 B2
APPLICATION NO.   : 13/309244
DATED             : February 11, 2014
INVENTOR(S)       : Xavier M. Colonna De Lega Page 1 of 1

It is certified that error appears in the above-identified patent and that said Letters Patent is hereby corrected as shown below:

On Title Page 2, item (56)
Column 2 (Other Publications), line 2, delete "light structured" and insert -- structured --

In the Claims

Column 22
Line 5, In Claim 21, delete "it" and insert -- $\pi$ --

Signed and Sealed this
Thirteenth Day of May, 2014

Michelle K. Lee
*Deputy Director of the United States Patent and Trademark Office*